(12) United States Patent
Feng et al.

(10) Patent No.: US 9,192,649 B2
(45) Date of Patent: Nov. 24, 2015

(54) ANNEXIN AND ITS USE TO TREAT INFLAMMATORY DISORDERS

(75) Inventors: Qingping Feng, London (CA); Xiangru Lu, London (CA); Paul Arnold, London (CA)

(73) Assignee: LONDON HEALTH SCIENCES CENTRE RESEARCH INC., London, Ontario (CA)

( * ) Notice: Subject to any disclaimer, the term of this patent is extended or adjusted under 35 U.S.C. 154(b) by 227 days.

(21) Appl. No.: 13/124,330

(22) PCT Filed: Oct. 16, 2009

(86) PCT No.: PCT/CA2009/001469
§ 371 (c)(1),
(2), (4) Date: Oct. 5, 2011

(87) PCT Pub. No.: WO2010/043045
PCT Pub. Date: Apr. 22, 2010

(65) Prior Publication Data
US 2012/0014920 A1    Jan. 19, 2012

Related U.S. Application Data

(60) Provisional application No. 61/106,390, filed on Oct. 17, 2008.

(51) Int. Cl.
| | | |
|---|---|---|
| A61K 38/12 | (2006.01) | |
| A61K 38/00 | (2006.01) | |
| C07K 14/47 | (2006.01) | |
| A61K 38/17 | (2006.01) | |

(52) U.S. Cl.
CPC .................................. *A61K 38/1709* (2013.01)

(58) Field of Classification Search
None
See application file for complete search history.

(56) References Cited

U.S. PATENT DOCUMENTS

| | | |
|---|---|---|
| 5,834,196 A | 11/1998 | Reutelingsperger |
| 2003/0152513 A1 | 8/2003 | Blankenberg et al. |
| 2005/0164926 A1 | 7/2005 | Wun |

FOREIGN PATENT DOCUMENTS

| | | |
|---|---|---|
| EP | 0 339 285 A2 | 11/1989 |
| EP | 0 496 013 A1 | 7/1992 |
| JP | 2-200188 | 8/1990 |
| JP | 4-266899 | 9/1992 |
| WO | 2005/099744 A1 | 10/2005 |
| WO | 2008/008561 A2 | 1/2008 |
| WO | 2009/001224 A2 | 12/2008 |
| WO | 2009/077764 A1 | 6/2009 |
| WO | 2009/103977 A1 | 8/2009 |

OTHER PUBLICATIONS

Cederholm et al. Annexin A5 in cardiovascular disease and systemic lupus erythematosus . Immunobiology. 2005;210(10):761-8. Epub Oct. 20, 2005.*

Van Heerde et al., Arterioscler Thromb. May 1994;14(5):824-30. Annexin V inhibits the procoagulant activity of matrices of TNF-stimulated endothelium under blood flow conditions.*

Sato et al Annexin V inhibits lipopolysaccharide-induced procoagulant activity on human monocytes. Thrombosis Research (2004) 114, 45-49.*

T. Pernerstorfer et al, Endotoxin-Induced Activation of the Coagulation Cascade in Humans, Effect of Acetylsalicylic Acid and Acetaminophen. Arterioscler Thromb Vasc Biol. 1999;19:2517-2523).*

Palmi, et al., "Inhibition of interleukin-1[beta]-induced pyresis in the rabbit by peptide 204-212 of lipocortin 5", European Journal of Pharmacology, vol. 281, No. 1, Jul. 1, 1995, pp. 97-99, XP55042604.

Sohn, et al., "Novel transglutaminase inhibitors reverse the inflammation of allergic conjunctivitis", Journal of Clinical Investigation, American Society for Clinical Investigation, US, vol. 111, No. 1, Jan. 1, 2003, pp. 121-128, XP002984889.

Perretti, et al., "A Novel Anti-Inflammatory Peptide from Human Lipocortin 5", British Journal of Pharmacology, vol. 103, No. 2, 1991, pp. 1327-1332.

European Search Report dated Nov. 7, 2012 for European Application No. EP 09 82 0159.

Angus, et al. "Epidemiology of sepsis: An update." 2001. Crit Care Med 29(7): S109-S116.

Angus, et al. "Epidemiology of severe sepsis in the United States: Analysis of incidence, outcome, and associated costs of care." 2001. Crit Care Med 29(7): 1303-1310.

Court, et al. "Clinical review: Myocardial depression in sepsis and septic shock." Dec. 2002. Critical Care 6(6): 500-508.

Damazo, et al. "Critical protective role for annexin 1 gene expression in the endotoxemic murine microcirculation." Jun. 2005. American Journal of Pathology 166(6): 1607-1617.

Geoghegan-Morphet, et al. "Role of neuronal nitric oxide synthase in lipopolysaccharide-induced tumor necrosis factor-alpha expression in neonatal mouse cardiomyocytes." 2007. Cardiovascular Research 75: 408-416.

Gerke, et al. "Annexins: From structure to function." 2002. The American Physiological Society 82: 331-371.

Grandel, et al. "Endotoxin-induced myocardial tumor necrosis factor-α synthesis depresses contractility of isolated rat hearts." 2000. Circulation American Heart Association 102: 2758-2764.

Hammoud, et al. "Endothelial nitric oxide synthase promotes neonatal cardiomyocyte proliferation by inhibiting tissue inhibitor of metalloproteinase-3 expression." 2007. Cardiovascular Research 75: 359-368.

Kapadia, et al. "Tumor necrosis factor-α gene and protein expression in adult feline myocardium after endotoxin administration." Aug. 1995. The Journal of Clinical Investigation, Inc. 96: 1042-1052.

(Continued)

*Primary Examiner* — Kagnew H Gebreyesus
(74) *Attorney, Agent, or Firm* — Knobbe, Martens, Olson & Bear, LLP

(57) ABSTRACT

There is provided a composition comprising an effective amount of Annexin A5 for use in treatment of an inflammatory disorder. There is provided a composition comprising an effective amount of Annexin A5 for use in improving organ function. Methods for administering such compositions for treatment of animals are also provided.

23 Claims, 7 Drawing Sheets

(56) References Cited

OTHER PUBLICATIONS

Markoff, et al. "Annexin A5 interacts with polycystin-1 and interferes with the polycystin-1 stimulated recruitment of E-cadherin into adherens junctions." 2007. Journal of Mol. Biol. 369: 954-966.

Martin, et al. "The Epidemiology of sepsis in the United states from 1979 through 2000." Apr. 17, 2003. The New England Journal of Medicine 348: 1546-1554.

Natanson, et al. "Endotoxin and tumor necrosis factor challenges in dogs simulate the cardiovascular profile of human septic shock." Mar. 1989. The Journal of Experimental Medicine 169: 823-832.

Parrillo, et al. "A circulating myocardial depressant substance in humans with septic shock." Oct. 1985. The Journal of Clinical Investigation, Inc. 75: 1539-1553.

Parrillo, et al. "Septic shock in humans: Advances in the understanding of pathogenesis, cardiovascular dysfunction, and therapy." Aug. 1990. Annals of Internal Medicine 113(3): 227-242.

Peng, et al. "Endothelial nitric-oxide synthase enhances lipopolysaccharide-stimulated tumor necrosis factor-$\alpha$ expression via cAMP-mediated p38 MAPK pathway in cardiomyocytes." Mar. 7, 2003. The Journal of Biological Chemistry 278(10): 8099-8105.

Peng, et al. "Inhibition of p38 MAPK decreases myocardial TNF-alpha expression and improves myocardial function and survival in endotoxemia." 2003. Cardiovascular Research 59: 893-900.

Peng, et al. "JNK1/c-fos inhibits cardiomyocyte TNF-$\alpha$ expression via a negative crosstalk with ERK and p38 MAPK in endotoxaemia." 2009. Cardiovascular Research 81: 733-741.

Peng, et al. "Pivotal Role of gp91phox--containing NADH oxidase in lipopolysaccharide-induced tumor necrosis factor-$\alpha$ expression and myocardial depression." Apr. 5, 2005. Circulation, American Heart Association, pp. 1637-1644.

Remick, et al. "Comparison of the mortality and inflammatory response of two models of sepsis: Lipopolysaccharide vs. cecal ligation and puncture." Feb. 2000. Shock 13(2): 110-116.

Reutelingsperger, et al. "Annexin V, the regulator of phosphatidylserine-catalyzed inflammation and coagulation during apoptosis." 1997. Cellular and Molecular Life Sciences 53: 527-532.

Soffreoini, et al. "The Cardiovascular response of normal humans to the administration of endotoxin." Aug. 3, 1989. The New England Journal of Medicine 321(5): 280-287.

Bouter, et al., "Annexin-A5 assembled into two-dimensional arrays promotes cell membrane repair", Nature Communications, Apr. 5, 2011, in 9 pages.

Jaimes, et al., "Unfractioned heparin for treatment of sepsis: A randomized clinical trial (The HETRASE Study)", Critical Care Medicine, 2009, vol. 37, No. 4, pp. 1185-1196.

Warren, et al., "High-Dose Antithrombin III in Severe Sepsis, A Randomized Controlled Trial", JAMA, Oct. 17, 2001, vol. 286, No. 15, pp. 1869-1878.

Dellinger, et al., "Surviving Sepsis Campaign: International Guidelines for Management of Severe Sepsis and Septic Shock: 2012", Special Articles, Feb. 2013, vol. 41, No. 2, pp. 580-637.

Zeiher, et al., "LY315920NA/S-5920, a selective inhibitor of group IIA secretory phospholipase A2, fails to improve clinical outcome for patients with severe sepsis", Critical Care Medicine, 2005, vol. 33, No. 8, pp. 1741-1748.

Zimmerman, et al., "DIC sepsis", Critical Care Medicine, Oct. 2013, vol. 41, No. 10, pp. e291-e292.

Morris, "Carrageenan-Induced aw Edema in the Rat and Mouse", Methods in Molecular Biology, 2003, vol. 225, pp. 115-121.

Bernard, et al. "The Effects of Ibuprofen on the Physiology and Survival of Patients with Sepsis", New Eng J of Med, 1997, vol. 336, pp. 912-918.

Tait et al. "Phospholipid binding properties of human placental anticoagulant protein-I, a member of the lipocortin family.", J. Biol. Chem. 1989, Vo.. 264, pp. 7944-7949.

Kang, et al., "Protection against lipopolysaccharide-induced sepsis and inhibition of interleukin-1B and prostaglandin E2 synthesis by silymarin", Biochemical Pharmacology 67 (2004) 175-181.

Wu et al., "Therapeutic effects of melatonin on perionitis-induced septic shock with multiple organ dysfunction syndrome in rats," J. Pineal Res. 2008; 45:106-116.

Definition of Dysfunction, Shorter Oxford English Dictionary excerpt, 1973.

Antiphospholipid syndrome, Wikipedia, extracted from the WayBack Machine Internet archive dated Oct. 19, 2007, 4 pages.

Atherosclerosis, Wikipedia, extracted from the WayBack Machine internet archive dated Oct. 11, 2007, 8 pages.

Restenosis, Wikipedia, extracted from the WayBack Machine Internet archive dated Jun. 14, 2007, 1 page.

Nephrotic syndrome, Wikipedia, extracted from the WayBack Machine internet archive dated Oct. 20, 2007, 4 pages.

Communication pursuant to Rule 114(2) EPC, dated Apr. 7, 2015 in European Patent Application No. 09820159.3.

\* cited by examiner

ANNEXIN AND ITS USE TO TREAT INFLAMMATORY DISORDERS

REFERENCE TO SEQUENCE LISTING

The present application incorporates by reference the Sequence Listing submitted as an ASCII text filed via EFS-Web. The Sequence Listing is provided as a file entitled 17085392.txt, created on Jan. 22, 2014, which is 6.32 Kb in size.

FIELD OF THE INVENTION

The present invention relates to treatment of inflammatory disorders. More particularly, the present invention relates to use of Annexin A5 for treatment of inflammatory disorders and in aspects, treatment of sepsis.

BACKGROUND OF THE INVENTION

Throughout this application, various references are cited in parentheses to describe more fully the state of the art to which this invention pertains. Full bibliographic information for each citation is found at the end of the specification, immediately preceding the claims. The disclosure of these references are hereby incorporated by reference into the present disclosure in their entirety.

Abnormalities associated with inflammation comprise a large group of disorders which underly a variety of human diseases. The immune system is often involved with inflammatory disorders, demonstrated in both allergic reactions and some myopathies, with many immune system disorders resulting in abnormal inflammation. Non-immune diseases with aetiological origins in inflammatory processes are thought to include sepsis, cancer, atherosclerosis, and ischaemic heart disease.

A large variety of proteins are involved in inflammation, and altered expression and/or activity of one or more of these proteins can impair or otherwise dysregulate the normal immune function.

Vertebrates achieve internal homeostasis during infection or injury by balancing the activities of proinflammatory and anti-inflammatory pathways. However, in many disease conditions, this internal homeostasis becomes out of balance. For example, endotoxin (lipopolysaccharide, LPS) produced by all Gram-negative bacteria activates macrophages to release cytokines that are potentially lethal (Tracey, K. J. et al., Science, 234:470-74 (1986); Dinarello, C. A., FASEB J., 8: 1314-25 (1994); Wang, H., et al., Science, 285:248-51 (1999); Nathan, C. F., J. Clin. Invest., 79:319-26 (1987)).

Inflammatory disorders (such as septic shock caused by endotoxin exposure) are often induced by pro-inflammatory cytokines, such as tumor necrosis factor (TNF; also known as TNFα or cachectin), interleukin (IL)-Ia, IL-I β, IL-6, IL-8, IL-18, interferonγ, platelet-activating factor (PAF), macrophage migration inhibitory factor (MIF), and other compounds. Pro-inflammatory cytokines contribute to various disorders through their release during an inflammatory cytokine cascade.

Therefore, there is a need for a treatment for inflammatory disorders.

SUMMARY OF THE INVENTION

In an aspect, there is provided a composition comprising an effective amount of Annexin A5 for use in treatment of an inflammatory disorder.

According to an aspect of the invention is a therapeutic pharmaceutical composition comprising an effective amount of Annexin A5 for treatment of an inflammatory disorder.

In another aspect, there is provided a composition comprising an effective amount of Annexin A5 for use in treatment of organ dysfunction.

In another aspect, there is provided a therapeutic pharmaceutical composition comprising an effective amount of Annexin A5 for use in treatment of sepsis.

In another aspect, there is provided a composition comprising an effective amount of Annexin A5 for use in the improvement of cardiac function during endotoxemia.

In any of the compositional or medicament aspects of the invention, the composition may further comprise one or more pharmaceutical agents.

In yet another aspect, there is a use of Annexin A5 for preparation of a medicament.

In a further aspect, there is provided a use of Annexin A5 for preparation of a medicament for treatment of an inflammatory disorder.

In still a further aspect, there is provided a use of Annexin A5 for preparation of a medicament for treatment of organ dysfunction, in aspects, cardiac dysfunction.

In a further aspect, there is provided a use of Annexin A5 for preparation of a medicament for treatment of sepsis in a subject.

In an even further aspect, there is provided a method of treating an inflammatory disorder in a subject comprising administering an effective amount of Annexin A5 to the subject.

In another aspect, there is provided a method for treatment of organ dysfunction in a subject comprising administering an effective amount of Annexin A5 to the subject.

According to another aspect of the present invention there is provided a method for the treatment of sepsis in a subject, the method comprising administering an effective amount of an Annexin to said mammal. In aspects, the Annexin is Annexin A5.

In yet another aspect, there is provided a use of Annexin A5 for preparation of a medicament for improving organ function in a subject.

In even another aspect, there is provided a composition comprising an effective amount of Annexin A5 for improving organ function.

In still another aspect, there is provided a method for improving organ function in a subject comprising administering an effective amount of Annexin A5 to the subject.

In a further aspect, there is provided a kit comprising Annexin A5 and a pharmaceutically acceptable carrier, and instructions for preparing a medicament comprising Annexin A5 and/or instructions for administering Annexin A5 for treatment of an inflammatory disorder.

In still a further aspect, there is provided there is provided a kit comprising Annexin A5 and a pharmaceutically acceptable carrier, and instructions for preparing a medicament comprising Annexin A5 and/or instructions for administering Annexin A5 for treatment of organ dysfunction in a subject.

BRIEF DESCRIPTION OF THE DRAWINGS

Embodiments will now be described, by way of example only, with reference to the attached Figures, wherein.

DETAILED DESCRIPTION OF THE INVENTION

Figure 1:
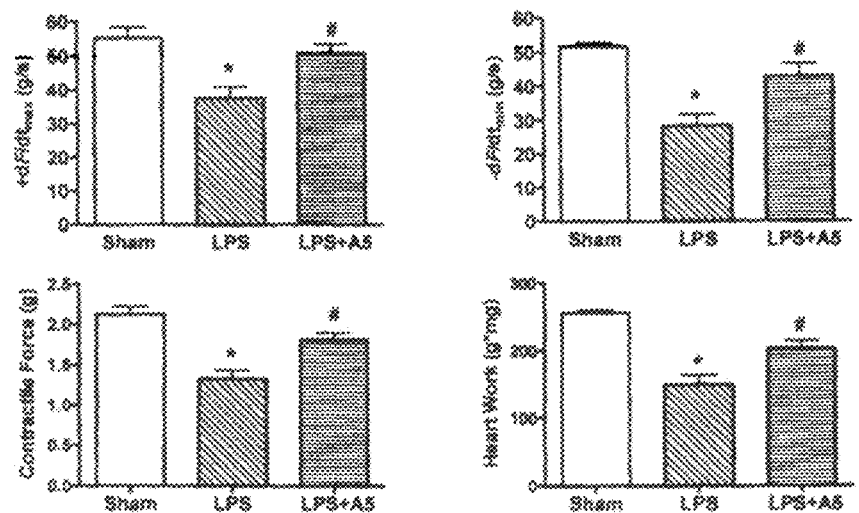
FIG. 1 shows an effect of Annexin A5 administration on cardiac function in mice with endotoxemia.

Methods and compositions for treatment of inflammatory disorders are described herein. More specifically, methods and compositions comprising use of Annexin A5 for treatment of inflammatory disorders are described herein. In aspects, the disorder is sepsis.

As used herein, "treatment" includes prophylactic and therapeutic treatment. "Prophylactic treatment" refers to treatment of a subject before onset of an inflammatory condition to prevent, inhibit or reduce its occurrence. Therapeutic treatment is treatment of a subject who is already experiencing an inflammatory disorder.

A "subject" may be any vertebrate animal, but will typically pertain to a mammal, for example a human patient, a domesticated animal (such as dog or cat), a farm animal (such as horse, cow, or sheep) or a laboratory animal (such as rat, mouse, non-human primate or guinea pig). In certain examples, the subject is human.

Inflammatory disorders" are usually mediated by an inflammatory cytokine cascade, defined herein as an in vivo release from cells of at least one proinflammatory cytokine in a subject, wherein the cytokine release affects a physiological condition of the subject. Non-limiting examples of cells that produce proinflammatory cytokines are monocytes, macrophages, neutrophils, epithelial cells, osteoblasts, fibroblasts, smooth muscle cells, and neurons.

A "cytokine" is a soluble protein or peptide which is naturally produced by mammalian cells and which act in vivo as humoral regulators at micro- to picomolar concentrations. Cytokines can, either under normal or pathological conditions, modulate the functional activities of individual cells and tissues. A proinflammatory cytokine is a cytokine that is capable of causing any of the following physiological reactions associated with inflammation: vasodialation, hyperemia, increased permeability of vessels with associated edema, accumulation of granulocytes and mononuclear phagocytes, or deposition of fibrin. Non-limiting examples of proinflammatory cytokines are tumor necrosis factor alpha (TNF), interleukin (IL)-Ia, IL-I-beta, IL-6, IL-8, IL-18, interferon-gamma, HMG-1, platelet-activating factor (PAF), and macrophage migration inhibitory factor (MIF). Proinflammatory cytokines can mediate deleterious conditions for many inflammatory disorders, for example endotoxic shock, asthma, rheumatoid arthritis, inflammatory bile disease, heart failure, and allograft rejection.

Proinflammatory cytokines are to be distinguished from anti-inflammatory cytokines, such as IL-4, IL-10, and IL-13, which are not mediators of inflammation. In certain examples, release of anti-inflammatory cytokines is not inhibited by the Annexin A5 treatment described herein.

In certain examples, the Annexin A5 treatment described herein inhibits the proinflammatory effect of TNF. TNF serves as a mediator in various inflammatory disorders. A few such examples include: septic shock, cancer, AIDS, transplantation rejection, multiple sclerosis, diabetes, rheumatoid arthritis, trauma, malaria, meningitis, ischemia-reperfusion injury, and adult respiratory distress syndrome.

TNF plays a role in several inflammatory disorders, and thus research has been conducted concerning TNF therapies and anti-TNF therapies. Research has focused upon inhibition of TNF activity in such inflammatory disorders as rheumatoid arthritis, Crohn's disease, AIDS, bacterial septic shock (caused by certain gram negative bacteria), and bacterial toxic shock (caused by superantigens) as well as in prevention of alloreactivity and graft rejection. Mutant mice that lack TNF are resistant to gram-negative bacteria induced sepsis (Janeway, C., Travers, P., Walport, M., Capra, J. Immunobiology: The Immune System in Health and Disease. New York, N.Y.: Garland Publishers. 1999), and anti-TNF monoclonal antibodies have been used to inhibit TNF activity and treat endotoximia (Beutler, B., Milsark, L., Cerami, A. 1985. Passive Immunization Against Cachectin/Tumor Necrosis Factor Protects Mice from Lethal Effects of Endotoxin. Science 229; 867-871). One advantage of treatment to control TNF activity results from its role in multiple types of inflammation. For example, it is often difficult to determine that inflammation in burn and trauma victims are of infectious etiology and warrant treatment with antibiotics; therefore treatment to inhibit TNF activity may be beneficial. Strategies for inhibition of TNF activity include neutralization of the cytokine via either anti-TNF antibodies, soluble receptors, or receptor fusion proteins; suppression of TNF-A synthesis via drugs such as cyclosporine A, glucocorticoids, or cytokine IL-10; reduction of responsiveness to TNF via repeated low dose stimulation; or by inhibition of secondary mediators such as IL-1, IL-6, or nitric oxide. Annexin A5 treatment described herein can be used to inhibit TNF activity.

When referring to the effect of Annexin A5 on an inflammatory disorder, the use of the terms "treatment", "inhibition", "reduction" or "attenuation" encompasses at least a small but measurable decrease in the symptoms associated with the disorder being treated as a result of Annexin A5 administration.

An inflammatory disorder can be one where an inflammatory cytokine cascade causes a systemic reaction, such as with systemic inflammatory response syndrome (SIRS) or septic shock. Alternatively, the disorder can be mediated by a localized inflammatory cytokine cascade, as in rheumatoid arthritis. Non-limiting examples of conditions which can be usefully treated using the Annexin A5 treatment described herein include appendicitis, peptic ulcer, gastric ulcer, duodenal ulcer, peritonitis, pancreatitis, ulcerative colitis, pseudomembranous colitis, acute colitis, ischemic colitis, diverticulitis, epiglottitis, achalasia, cholangitis, cholecystitits, hepatitis, Crohn's disease, enteritis, Whipple's disease, allergy, anaphylactic shock, immune complex disease, multiple organ dysfunction syndrome (MODS), organ ischemia, reperfusion injury, organ necrosis, hay fever, systemic inflammatory response syndrome (SIRS), sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, pneumonitits, alvealitis, bronchiolitis, pharyngitis, pleurisy, sinusitis, influenza, respiratory syncytial virus infection, HIV infection, AIDS, hepatitis B virus infection, hepatitis C virus infection, herpes virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thyroiditis, systemic lupus erythematosis, Goodpasture's syndrome, Behcet's syndrome, allograft rejection, graft-versus-host disease, Type I diabetes, obesity, ankylosing spondylitis, Berger's disease, Reiter's syndrome and Hodgkin's disease.

In certain non-limiting examples, the inflammatory disorder is selected from asthma, allergy, anaphylactic shock, multiple organ dysfunction syndrome (MODS), organ ischemia, ischaemia-reperfusion injury, organ necrosis, SIRS, sepsis, septicemia, endotoxic shock, cachexia, septic abortion, disseminated bacteremia, burns, coeliac disease, congestive heart failure, myocarditis, myocardial ischemia adult respiratory distress syndrome, cerebral infarction, cerebral embolism, spinal cord injury, paralysis, allograft rejection or graft-versus-host disease.

In one example, the inflammatory disorder is endotoxic shock. In another example, the inflammatory disorder is SIRS. In still another example, the inflammatory disorder is sepsis. In yet another example, the inflammatory disorder is multiple organ dysfunction syndrome (MODS).

Annexin A5 that may be used to improve organ function (for example, heart, liver, lung, kidney, or brain) during sepsis. Annexin A5 may also be used to treat systemic organ injuries during systemic inflammatory response syndrome (SIRS) and trauma, or injuries involving ischemia and reperfusion.

Sepsis is a systemic inflammatory response to infection and the most common cause of death in intensive care units. Mortality is 20-30% in sepsis and 40-80% in septic shock [1]. Myocardial dysfunction is a common complication of septic shock [2]. This systemic inflammatory disorder is a result of a dysregulated host response to infection and is characterized by excessive pro-inflammatory cytokine production. Initiation of the host's innate immune response is mediated through the activation of the cell membrane toll-like receptor-4 (TLR4) in recognizing pathogen-associated molecular patterns (PAMPs). Lipopolysaccharide (LPS) is the most prominent PAMP in the outer membrane of Gram-negative bacteria and binds to TLR4 in a CD-14 and LPS binding protein (LBP) dependent manner. Activation of TLR4 upon LPS binding initiates a signalling pathway that leads to the activation of the mitogen-activated protein kinases (MAPK) and production of TNF, a prominent cytokine which is a major contributing factor in organ dysfunction (for example, cardiac dysfunction) in sepsis [3, 4].

Sepsis is considered present if infection is highly suspected or proven and two or more of the following systemic inflammatory response syndrome (SIRS) criteria are met (Bone R C, Balk R A, Cerra F B, et at (June 1992). "Definitions for sepsis and organ failure and guidelines for the use of innovative therapies in sepsis. The ACCP/SCCM Consensus Conference Committee. American College of Chest Physicians/Society of Critical Care Medicine". Chest 101 (6): 1644-55.):

Heart rate >90 beats per minute (tachycardia);

Body temperature <36° C. (96.8° F.) or >38° C. (100.4° F.) (hypothermia or fever);

Respiratory rate >20 breaths per minute or, on blood gas, a PaCO2 less than 32 mm Hg (4.3 kPa) (tachypnea or hypocapnia due to hyperventilation);

White blood cell count <4000 cells/mm$^3$ or >12000 cells/mm$^3$ (<4×10$^9$ or >12×10$^9$ cells/L), or greater than 10% band forms (immature white blood cells); (leukopenia, leukocytosis, or bandemia).

Fever and leukocytosis are features of the acute phase reaction, while tachycardia is often the initial sign of hemodynamic compromise. Tachypnea may be related to the increased metabolic stress due to infection and inflammation, but may also be a sign of inadequate perfusion resulting in the onset of anaerobic cellular metabolism.

In children, the SIRS criteria are modified in the following fashion (Goldstein B, Giroir B, Randolph A (2005). "International pediatric sepsis consensus conference: definitions for sepsis and organ dysfunction in pediatrics". Pediatr Crit Care Med 6 (1): 2-8):

Heart rate >2 standard deviations above normal for age in the absence of stimuli such as pain and drug administration, OR unexplained persistent elevation for greater than 30 minutes to 4 hours. In infants, also includes Heart rate <10th percentile for age in the absence of vagal stimuli, beta-blockers, or congenital heart disease OR unexplained persistent depression for greater than 30 minutes;

Body temperature obtained orally, rectally, from Foley catheter probe, or from central venous catheter probe >38.5° C. or <36° C. Temperature must be abnormal to qualify as SIRS in pediatric patients;

Respiratory rate >2 standard deviations above normal for age OR the requirement for mechanical ventilation not related to neuromuscular disease or the administration of anesthesia;

White blood cell count elevated or depressed for age not related to chemotherapy, or greater than 10% bands+ other immature forms.

As will be recognized by the skilled person SIRS criteria must be interpreted carefully within the clinical context. These criteria exist primarily for the purpose of more objectively classifying critically-ill patients so that future clinical studies may be more rigorous and more easily reproducible.

Consensus definitions continue to evolve with the latest list of signs and symptoms of sepsis to reflect clinical bedside experience.

To qualify as sepsis, there must be an infection suspected or proven (by culture, stain, or polymerase chain reaction (PCR)), or a clinical syndrome pathognomonic for infection. Specific evidence for infection includes WBCs in normally sterile fluid (such as urine or cerebrospinal fluid (CSF), evidence of a perforated viscus (free air on abdominal x-ray or CT scan, signs of acute peritonitis, abnormal chest x-ray (CXR) consistent with pneumonia (with focal opacification), or petechiae, purpura, or purpura fulminans The more critical subsets of sepsis are severe sepsis (sepsis with acute organ dysfunction) and septic shock (sepsis with refractory arterial hypotension). Alternatively, when two or more of the systemic inflammatory response syndrome criteria are met without evidence of infection, patients may be diagnosed simply with "SIRS." Patients with SIRS and acute organ dysfunction may be termed "severe SIRS."

Patients are defined as having "severe sepsis" if they have sepsis plus signs of systemic hypoperfusion: either organ dysfunction or a serum lactate greater than 4 mmol/dL. Other signs include oliguria and altered mental status. Patients have also been defined as having septic shock if they have sepsis plus hypotension after aggressive fluid resuscitation (typically upwards of 6 liters or 40 ml/kg of crystalloid).

Examples of end-organ dysfunction include the following (Abraham E, Singer M (2007). "Mechanisms of sepsis-induced organ dysfunction". Crit. Care Med. 35 (10): 2408-16):

Lungs—acute lung injury (ALI) ($PaO_2/FiO_2<300$) or acute respiratory distress syndrome (ARDS) ($PaO_2/FiO_2<200$);

Brain—encephalopathy—(symptoms: agitation, confusion, coma); (etiologies: ischemia, hemorrhage, microthrombi, microabscesses, multifocal necrotizing leukoencephalopathy);

Liver—disruption of protein synthetic function: manifests acutely as progressive coagulopathy due to inability to synthesize clotting factors; disruption of metabolic functions: manifests as cessation of bilirubin metabolism, resulting in elevated unconjugated serum bilirubin levels (indirect bilirubin);

Kidney—oliguria and anuria; electrolyte abnormalities; volume overload;

Heart—systolic and diastolic heart failure, at least in part due to cytokines that depress myocyte function; cellular damage, manifest as a troponin leak (although not necessarily ischemic in nature).

The Annexin A5 treatment described herein is not intended for treatment of a blood coagulation disorder such as disseminated intravascular coagulation (DIC). In certain examples, Annexin A5 is used to treat an inflammatory disorder, such as sepsis, at an early stage to prevent occurrence of a blood coagulation disorder such as disseminated intravascular coagulation (DIC).

Compositions and methods described herein will comprise an Annexin molecule, and more typically an Annexin polypeptide.

In one example, compositions comprising an Annexin A5 molecule are provided.

Annexin A5 is a 35 kDa phospholipid binding protein which is part of a 13 member protein family (Table 1, Gerke et al., Physiol Review 2002; 82:331-371). It binds to anionic phospholipids (eg. phosphatidylserine) on the plasma membrane in a calcium dependent manner and demonstrates anti-apoptotic and anti-coagulant properties by forming a protective 2D crystallized shield over the surface of cells where phosphatidylserine is exposed [Reutelingsperger et al., Cell Mol Life Sci 1997; 53:527-532]. This protective shield sequesters the phospholipid sites where extracellular factors complex and decreases their ability to initiate phagocytosis or thrombosis.

Annexin A5 is used in some diagnostic methods and products, with some examples provided by the following companies:

Affinity Research, UK; Annexin A5—identifying the dying cell;

Bender MedSystems GmbH, D; Bender MedSystems GmbH through Boehringer Ingelheim holds manufacturing rights for Annexin A5, and offers a wide range of different formats and conjugates of Annexin A5 products;

Caltag Laboratories, Burlingame, Calif., USA; Human recombinant annexin A5;

Clontech, Palo Alto, Calif.; ApoAlert Annexin A5 Protocols;

IQ Products, Groningen, NL; Annexin A5 for phosphatidylserine detection;

Oncogene Research Products; AnxA5-Biotin, AnxA5-FITC Apoptosis Detection Kit;

R&D Systems; AnxA5-Fluorescein, AnxA5-Phycoerythrin;

Tau Technologies BV, NL; anti-Annexin A5 antibody;

Trevigen, Md., USA; Annexin A5 apoptosis products: TAC5 AnxA5-FITC, TAC5 AnxA5-Biotin.

An early publication of a gene sequence of Annexin A5 is a disclosure in 1987 of endonexin II (Schaepfer et al. 1987. Structural and functional characterization of endonexin II, a calcium- and phospholipid-binding protein. PNAS USA 84: 6078-6082). An early publication of the protein is a disclosure in 1979 (Bohn, H and Kraus W. 1979. Isolation and characterization of a new placental specific protein (PP10). Arch Gynecol 227: 125-134).

Annexin A5 is also known as: placental anticoagulant protein I (Tait et al. Phospholipid binding properties of human placental anticoagulant protein-I, a member of the lipocortin family. J Biol Chem. 1989 May 15; 264(14):7944-9; Grundmann et al. Characterization of cDNA encoding human placental anticoagulant protein (PP4): homology with the lipocortin family. Proc Natl Acad Sci USA. 1988 June; 85(11): 3708-12); vascular anticoagulant-alpha (Andree et al. 1990. Binding of vascular anticoagulant alpha (VAC alpha) to planar phospholipid bilayers. J Biol Chem. 1990 Mar. 25; 265

(9): 4923-8); endonexin II (Schaepfer et al. 1987. Structural and functional characterization of endonexin II, a calcium- and phospholipid-binding protein. PNAS USA 84: 6078-6082); lipocortin V (Rothhut et al. A 32 kDa lipocortin from human mononuclear cells appears to be identical with the placental inhibitor of blood coagulation. Biochem J. 1989 Nov. 1; 263(3): 929-35); placental protein 4 (Inaba et al. Clinical significance of a new membrane associated placental protein 4 (PP4) in gynecologic malignancies. Nippon Sanka Fujinka Gakkai Zasshi. 1986 February; 38(2):265-6); and anchorin CII (Mollenhauer et al. Role of anchorin CII, a 31,000-mol-wt membrane protein, in the interaction of chondrocytes with type II collagen. J Cell Biol. 1984 April; 98(4): 1572-9; von der Mark et al. Anchorin CII, a type II collagen-binding glycoprotein from chondrocyte membranes. Ann NY Acad Sci. 1985; 460:214-23; Mauch et al. A defective cell surface collagen-binding protein in dermatosparactic sheep fibroblasts. J Cell Biol. 1988 January; 106(1):205-11; Pilar et al. The structure of anchorin CII, a collagen binding protein isolated from chondrocyte membrane. J Biol Chem. 1988 Apr. 25; 263(12):5921-5).

Without wishing to be bound by theory, Annexin A5 treatment described herein is demonstrated to treat an inflammatory disorder by inhibition of a proinflammatory cytokine, such as TNFα. Annexin A5 treatment as described herein is not intended as an anti-coagulant. Accordingly, in certain examples Annexin A5 is used to treat organ dysfunction in an inflammatory disorder independent of an anti-coagulant effect.

Compositions comprising an Annexin A5 molecule may be useful to treat an inflammatory disorder. Compositions comprising an Annexin A5 molecule may be useful to improve organ function (for example, heart, liver, lung, kidney, or brain) in a subject suffering from an inflammatory disorder. Compositions comprising an Annexin A5 molecule may also be useful to treat an inflammatory disorder associated with production of a cytokine (for example, TNFα). Compositions comprising an Annexin A5 molecule may also be useful for treatment of organ (for example, heart, liver, lung, kidney, or brain) dysfunction or injury during SIRS or sepsis. Compositions comprising an Annexin A5 molecule may also be useful for treatment of organ (for example, heart, liver, lung, kidney, or brain) dysfunction or injury during ischemia or reperfusion. Compositions comprising an Annexin A5 molecule may also be useful for treatment of sepsis to prevent occurrence of DIC.

Compositions comprising an Annexin A5 molecule may be used to treat any disorder where the inhibition of a proinflammatory cytokine provides a prophylactic and/or therapeutic benefit. Accordingly, a method for treating an inflammatory disorder in a subject comprises administering an amount of Annexin A5 molecule effective to inhibit activity of a proinflammatory cytokine (for example, TNF-α).

Without limitation, the Annexin A5 molecule may be a full-length naturally occurring polypeptide or a variant thereof, or may be a nucleic acid molecule encoding an Annexin A5 polypeptide or variant thereof. Furthermore, a recombinant cell producing the Annexin A5 molecule is provided.

An Annexin A5 polypeptide may be provided by any source or method, for example, natural isolate or recombinant or synthetic origin or suitable combinations thereof. Administration of the Annexin A5 polypeptide to a subject can be used to treat an inflammatory disorder, and more specifically to treat organ dysfunction in an inflammatory disorder. The Annexin A5 polypeptide will be administered in an amount effective to inhibit a proinflammatory cytokine, such as TNFα. The Annexin A5 polypeptide may be of any length provided that its anti-inflammatory activity is maintained. The sequence of the Annexin A5 polypeptide may be based on a complete or partial naturally occurring amino acid sequence. The Annexin A5 polypeptide may be used either singly or in combination with other polypeptides, anti-inflammatory or otherwise, in the preparation of a composition that treats an inflammatory disorder or treats organ dysfunction in an inflammatory disorder. A polypeptide refers to a chain of amino acids, for example peptides, oligopeptides, or proteins, having a biological function, and does not refer to a specific length of the chain.

An isolated Annexin A5 polypeptide is a polypeptide that has been identified and separated and/or recovered from at least one component of its natural environment. The isolated polypeptide will typically have been purified by at least one purification step, and, in some embodiments purification may be achieved (1) to a degree sufficient to obtain at least 15 residues of N-terminal or internal amino acid sequence by use of a sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the Annexin A5 polypeptide natural environment will not be present. An isolated polypeptide may be produced by synthetic or recombinant techniques, for example as described in J. Sambrook, E. F. Fritsch, and T. Maniatis, 1989, Molecular Cloning: A Laboratory Manual, Second Edition, Books 1-3, Cold Spring Harbor Laboratory Press. An isolated polypeptide produced as a result of recombinant techniques may be referred to as a recombinant polypeptide.

A nucleic acid encoding an Annexin A5 polypeptide may be any nucleic acid molecule of, for example. cDNA, genomic DNA, synthetic DNA or RNA origin or suitable combinations thereof. Administration of the nucleic acid encoding an Annexin A5 polypeptide to a subject can be used to treat an inflammatory disorder, and more specifically to treat organ dysfunction in an inflammatory disorder. The Annexin A5 nucleic acid will be administered in an amount effective to inhibit a proinflammatory cytokine, such as TNF. The nucleic acid may be of any length provided that the anti-inflammatory activity is maintained by the encoded Annexin A5 polypeptide. The sequence of the nucleic acid encoding an Annexin A5 polypeptide may be based on a complete or partial naturally occurring nucleic acid sequence. A nucleic acid sequence encoding an Annexin A5 polypeptide may be used either singly or in combination with other nucleic acid sequences, encoding anti-inflammatory polypeptides or encoding any other desired polypeptide, in the preparation of a composition that treats an inflammatory disorder or treats organ dysfunction in an inflammatory disorder.

An isolated nucleic acid molecule encoding an Annexin A5 polypeptide is a nucleic acid molecule that is identified and separated from at least one contaminant nucleic acid molecule with which it is ordinarily associated in the natural source of the nucleic acid. Such an isolated nucleic acid molecule is other than in the form or setting in which it is found in nature. Isolated nucleic acid molecules therefore are distinguished from the nucleic acid molecule as it exists in natural cells. An isolated nucleic acid molecule encoding an Annexin A5 polypeptide includes nucleic acid molecule encoding an Annexin A5 polypeptide contained in cells that ordinarily express the Annexin A5 polypeptide where, for example, the nucleic acid molecule is in a chromosomal or extrachromosomal location different from that of natural cells. The isolated nucleic acid molecule may be referred to as a recombinant nucleic acid molecule where the isolated nucleic acid molecule has been manipulated using recombinant techniques, for example, as described in J. Sambrook, E. F. Fritsch, and T. Maniatis, 1989, Molecular Cloning: A Laboratory Manual, Second Edition, Books 1-3, Cold Spring Harbor Laboratory Press.

Variants include, without limitation, analogs, derivatives, fragments, truncations, splice variants, mutants, deletions, substitutions, insertions, fusions and the like.

An Annexin A5 polypeptide or a nucleic acid encoding an Annexin A5 polypeptide may be mutated or changed or derivatised in any manner desired (for example, any number or combination of deletions, insertions, or substitutions) to produce a corresponding variant. Use of such variants in treatment of an inflammatory disorder or treatment of organ dysfunction in an inflammatory disorder is contemplated, and such a variant nucleic acid or variant polypeptide may be mutated or changed or derivatised in any manner in comparison to a naturally occurring nucleic acid or polypeptide sequence, respectively, provided that the anti-inflammatory activity is maintained. Similarly, nucleic acids or polypeptides having varying degrees of sequence identity to a corresponding naturally occurring nucleic acid or polypeptide sequence may be tolerated without eliminating an anti-inflammatory activity. For example, a composition may comprise an Annexin A5 polypeptide having a sequence that is identical to a naturally-occurring form of the Annexin A5 polypeptide or a variant thereof that has a sequence that is at least 80% identical to a naturally-occurring form of the Annexin A5 polypeptide. As another example, a composition may comprise a nucleic acid molecule having a coding sequence that is identical to a naturally-occurring form of the coding sequence or a variant thereof that has a sequence that is at least 70% identical to a naturally-occurring form of the coding sequence. Determination of sequence identity of proteins and nucleic acids by computer based methods, as well as nucleic acid hybridization techniques using high stringency conditions for determining or identifying nucleic acid sequences that share high (eg., at least 70%) sequence identity are well known to the skilled person.

Stringency of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of sequence identity between the probe and hybridizable sequence, the higher the relative temperature which can be used. High stringency conditions may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. Hybridization and wash times should be sufficient for achieving equilibrium.

Percent (%) sequence identity of amino acid or nucleic acid sequences with respect to Annexin A5 polypeptides and nucleic acid sequences encoding Annexin A5 polypeptides is the percentage of residues in a candidate sequence that are identical with the Annexin A5 polypeptide amino acid sequence or the Annexin A5 polypeptide-encoding nucleic acid sequence, as the case may be, after aligning the sequences and introducing gaps, if necessary, to achieve the maximum percent sequence identity. Alignment for purposes of determining percent amino acid sequence identity or percent nucleic acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over a desired length of sequence, for example, at least 20, 30, 40, 50, 60, 70, 80, 90, 100, 110, 120, 130, 140, 150, 160, 170, 180, 190, or 200 residues or even the full-length of the sequences being compared.

When considering an Annexin A5 polypeptide or variant thereof, the variant annexin A5 polypeptide will typically have an amino acid sequence that is at least 80, 82, 84, 86, 88, 90, 92, 94, 96, or 98 percent identical to the corresponding Annexin A5 polypeptide.

When considering a nucleic acid sequence encoding an Annexin A5 polypeptide or variant thereof, the variant nucleic acid sequence will typically be at least 70, 72, 74, 76, 78, 80, 82, 84, 86, 88, 90, 92, 94, 96, or 98 percent identical to the corresponding nucleic acid encoding the Annexin A5 polypeptide.

Techniques and strategies for producing variants are well known in the art. In one example, with regard to polypeptides, an Annexin A5 polypeptide may be modified in vivo or in vitro by, glycosylation, amidation, phosphorylation, carboxylation, truncation, fragmentation, substitution, and the like without eliminating anti-inflammatory activity. In another example, with regard to nucleic acids, substitution mutations can be made in a nucleic acid encoding an Annexin A5 polypeptide such that a particular codon is changed to a codon which codes for a different amino acid. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e. by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. Groupings of amino acids are known to the skilled person. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charges (basic) amino acids include arginine, lysine and histidine. The negatively charged (acidic) amino acids include aspartic acid and glutamic acid. Any number of such substitutions or any other type of alteration (eg., deletion or insertion) or modification may be tolerated provided that the anti-inflammatory effect is not eliminated.

Recombinant cells, comprising an Annexin A5 polypeptide or a nucleic acid sequence that encodes an Annexin A5 polypeptide may be used for treatment of an inflammatory disorder or treatment of organ dysfunction in an inflammatory disorder. Recombinant cell types may include any cell type that is compatible with the physiology of an intended subject selected for treatment.

A cell may be altered or modified to comprise a nucleic acid sequence that does not naturally occur in the cell, and as such the cell will be considered recombinant. In other examples, a cell may be altered or modified to comprise an additional copy of a nucleic acid sequence that naturally occurs in the cell, and such cells will also be considered recombinant. As is understood by one of skill in the art, a nucleic acid encoding an Annexin A5 polypeptide may be introduced into a cell using any known technique, for example, microinjection, electroporation, viral transfection, lipofectamine transfection, calcium phosphate precipitation and the like. In certain non-limiting examples, a stem cell may be modified by introduction of a nucleic acid molecule encoding an Annexin A5 polypeptide, and then the modified cells may be administered to a subject. In certain other examples, a nucleic acid molecule encoding an Annexin A5 polypeptide may be incorporated into an appropriate construct or vehicle, for example a viral construct, and administered to a subject such that the nucleic acid molecule encoding the Annexin A5 polypeptide is introduced and expressed in at least a portion of the cells of the subject.

A nucleic acid encoding an Annexin A5 polypeptide may be operably linked to control sequences, typically in the context of a suitable vector. A useful control sequence may be any nucleic acid element that is necessary or advantageous for expression of the coding sequence of the nucleic acid sequence. Each control sequence may be native or foreign to the nucleic acid sequence encoding the Annexin A5 polypeptide. Such control sequences include, but are not limited to, a leader, a polyadenylation sequence, a propeptide sequence, a promoter, a signal sequence, or a transcription terminator. Alternatives for incorporating control sequences are readily available to the skilled person. For example, a nucleic acid encoding an Annexin A5 polypeptide may be under the control of an endogenous upstream promoter, or it may be put under control of a heterologous upstream promoter. Examples of suitable promoters for directing the transcription of an Annexin A5 nucleotide sequence in a bacterial host include the promoter of the lac operon of *E. coli*, the *Streptomyces coelicolor* agarase gene dagA promoters, the promoters of the *Bacillus licheniformis* alpha-amylase gene (amyl), the promoters of the *Bacillus stearothermophilus* maltogenic amylase gene (amyM), the promoters of the *Bacillus amyloliquefaciens* alpha-amylase gene (amyQ), the promoters of the *Bacillus subtilis* xylA and xylB genes, the promoter of the *Bacillus subtilis* aprE gene and a promoter derived from a *Lactococcus* sp.—derived promoter including the P170 promoter. When the nucleic acid encoding an Annexin A5 polypeptide is expressed in a bacterial species such as *E. coli*, a suitable promoter can be selected, for example, from a bacteriophage promoter including a T7 promoter and a phage lambda promoter.

For transcription in a fungal species, examples of useful promoters are those derived from the genes encoding the, *Aspergillus oryzoe* TAKA amylase, *Rhizomucor miehei* aspartic proteinase, *Aspergillus niger* neutral alpha-amylase, *A. niger* acid stable alpha-amylase, *A. niger* glucoamylase, *Rhizomucor miehei* lipase, *Aspergillus oryzoe* alkaline protease, *Aspergillus oryzoe* triose phosphate isomerase or *Aspergillus nidulons* acetamidase.

Examples of suitable promoters for the expression in a yeast species include but are not limited to the Gal 1 and Gal 10 promoters of *Saccharomyces cerevisiae* and the *Pichia pastoris* AOX1 or AOX2 promoters.

Still further suitable promoters are available to the skilled person, for example, cytomegalovirus, Rous Sarcoma Virus, synthetic pox viral promoter, pox synthetic late promoter 1, pox synthetic late promoter 2 early promoter 2, pox 01L promoter, pox 14L promoter, pox 13L promoter; pox 12L promoter, pox IIL promoter, pox DIOR promoter, PRV gX, HSV-1 alpha 4, chicken beta-actin promoter, HCMV immediate early, MDV gA, MDV gB, MDV gD, ILT gB, BHV-1.1 VP8 and ILT gD and internal ribosomal entry site promoter.

A suitable vector may be any vector (for example, a plasmid or virus) which can incorporate a nucleic acid sequence encoding an Annexin A5 polypeptide and any desired control sequences and can bring about the expression of the nucleic acid sequence. The choice of the vector will typically depend on the compatibility of the vector with a host cell into which the vector is to be introduced. In certain examples, the vector may exist as an extrachromosomal entity, with replication being independent of chromosomal replication, for example, a plasmid, an extrachromosomal element, a minichromosome, or an artificial chromosome. In other examples, the vector may be one which, when introduced into the host cell, is integrated into the genome and replicated together with the chromosome(s) into which it has been integrated. Still other examples of vectors and techniques for manipulating vectors will be known and apparent to the skilled person.

Recombinant cells may comprise an Annexin A5 polypeptide or a nucleic acid sequence encoding an Annexin A5 polypeptide, either singly or in combination, with other desired polypeptide or nucleic acid molecules, respectively, for example to optimize or enhance efficacy. Furthermore, a nucleic acid sequence may be mutated or altered prior to introduction into the cells as desired, for example for codon optimization for expression in a particular cell type. In addition, a nucleic acid sequence may be altered to encoded a fusion of an Annexin A5 polypeptide with one or more other polypeptide(s) as desired in an application, for example fusion with a targeting polypeptide or a carrier polypeptide.

The skilled person will recognize that variants described herein with respect to Annexin A5 molecules and cells comprising Annexin A5 molecules can apply equally to other polypeptides, nucleic acid molecules, and cells that are used in combination with Annexin A5 molecules and cells comprising Annexin A5 molecules. In certain examples, anti-inflammatory polypeptides, nucleic acid molecules encoding anti-inflammatory polypeptides or cells producing anti-inflammatory polypeptides may be used in combination with Annexin A5 molecules or cells producing Annexin A5 molecules. In certain examples, an Annexin A5 molecule is used in combination with an Annexin 1 molecule.

As is understood by the skilled person, administration of polypeptides, nucleic acid molecules, or cells can be done in a variety of manners. For example, administration may be done intramuscularly, subcutaneously, intravenously, intranasally, intradermaly, intrabursally, in ovo, ocularly, orally, intra-tracheally or intra-bronchially, as well as combinations of such modalities. The dose may vary with the size of the intended subject. Methods of administration are known to the skilled person, for example, see U.S. Pat. Nos. 5,693,622; 5,589,466; 5,580,859; and 5,566,064. The amounts of polypeptide, nucleic acid sequence, or recombinant cell needed for preparation of a composition is well understood by one of skill in the art.

Therapeutically effective amounts can also be determined in animal studies. The applied dose of Annexin A5 can be adjusted based on the relative bioavailability and potency of the administered compounds, including the adjuvants used. Adjusting the dose to achieve maximal efficacy based on the methods described above and other methods are well within the capabilities of the ordinarily skilled artisan. Subject doses of Annexin A5 as described herein may typically range from about 0.1 .µg to 10,000 mg, more typically from about 1 .µg/day to 8000 mg, even more typically from about 10 .µg to 5 mg, and most typically from about 10 µg to 100 pg. Stated in terms of subject body weight, typical dosages range from about 0.1 µg to 20 mg/kg/day, more typically from about 1 to 10 mg/kg/day, and most typically from about 1 to 5 mg/kg/day although daily doses may be more than 20 mg/kg/day or less than 0.1 .µg/kg/day. For example, in some embodiments, the Annexin A5 may be administered in amounts of less than or equal to 1.0 mg/kg per day. This includes amounts equal to or less than 0.9, 0.8, 0.7, 0.6, 0.5, 0.4, 0.3, 0.2, 0.1 mg/kg per day. The Annexin A5 may also be administered in amounts of less than or equal to 0.1 mg/kg per day (e.g., less than or equal to 0.09, 0.08, 0.07, 0.06, 0.5, 0.04, 0.03, 0.02 or 0.01 mg/kg/day). In some embodiments, the agents are administered in a range of about 0.005 mg/kg per day to less than 1.0 mg/kg per day (or about 0.005 mg/kg per day to equal to or less than 0.1 mg/kg per day). In some embodiments, more than 20 mg/kg/day In some embodiments (e.g., in methods particularly directed at subjects at risk of developing an inflammatory disorder), timing of the administration of an agent comprising Annexin A5 and/or functional equivalent may be important. For instance, a subject may be administered on a routine schedule. A "routine schedule" as used herein, refers to a predetermined designated period of time. The routine schedule may encompass periods of time which are identical or which differ in length, as long as the schedule is predetermined. For instance, the routine schedule may involve administration on a daily basis, every two days, every three days, every four days, every five days, every six days, a weekly basis, a monthly basis or any set number of days or weeks there-between, every two months, three months, four months, five months, six months, seven months, eight months, nine months, ten months, eleven months, twelve months, etc. Alternatively, the predetermined routine schedule may involve administration on a daily basis for the first week, followed by a monthly basis for several months, and then every three months after that. Any particular combination would be covered by the routine schedule as long as it is determined ahead of time that the appropriate schedule involves administration on a certain day.

Polypeptides, nucleic acids, or recombinant cells described herein, may be used in combination with a pharmaceutically acceptable carrier for preparation of a composition for treatment of an inflammatory disorder or treatment of organ dysfunction in an inflammatory disorder. Pharmaceutically acceptable carriers are well known to those skilled in the art and include but are not limited to proteins, sugars, and the like. One example of such a suitable carrier is a physiologically balanced culture medium containing one or more stabilizing agents such as hydrolyzed proteins, lactose, and the like. Another example of an acceptable carrier is 0.01-0.1M, and preferably 0.05M, phosphate buffer or 0.8% saline. Acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Examples of aqueous carriers are water, alcoholic/aqueous solutions, emulsions or suspensions, including saline and buffered media. Preservatives and other additives for pharmaceutical compositions are also well known to the skilled person, for example antimicrobials, antioxidants, chelating agents, inert gases, organic acids and the like. Another example of such a suitable carrier is a biomaterial comprising natural or synthetic extracellular matrix material.

Compositions of the invention comprising Annexin A5 may also include other pharmaceutical agents as desired for treatment of an inflammatory disorder. For example, but not limiting, in the treatment of sepsis the Annexin A5 composition may further comprise one or more antibiotics or vasopressors and/or corticosteroids as is used in the treatment of sepsis. Thus additional pharmaceuticals are selected based on the underlying condition to be treated.

Kits comprising polypeptides, nucleic acids, or recombinant cells described herein, in combination with a pharmaceutically acceptable carrier are contemplated. Kits will typically comprise instructions for preparing a medicament comprising Annexin A5 and/or instructions for administering Annexin A5 for improving organ function in a subject suffering from an inflammatory disorder.

When introducing elements disclosed herein, the articles "a", "an", "the", and "said" are intended to mean that there are one or more of the elements unless the context dictates otherwise. For example, the term "a compound" and "at least one compound" may include a plurality of compounds, including mixtures thereof. The terms "comprising", "having", "including" are intended to be open-ended and mean that there may be additional elements other than the listed elements. The phrase "consisting essentially of" is intended to be limiting to specified elements and those further elements that do not materially affect the basic and novel characteristic of the combination of specified elements. For example, a composition defined using the phrase "consisting essentially of" encompasses any known pharmaceutically acceptable additive, excipient, diluent, carrier, and the like.

The above detailed description is solely for purposes of illustration and is not intended to limit the scope of the claims. A more complete understanding can be obtained by reference to the following specific Examples. The Examples are also described solely for purposes of illustration and are not intended to limit the scope of the claims. Changes in form and substitution of equivalents are contemplated as circumstances may suggest or render expedient. Although specific terms have been employed herein, such terms are intended in a descriptive sense and not for purposes of limitation.

EXAMPLES

Example 1

Methods Used in Examples 2 and 3

Animals.

The investigation conforms with the Guide for the Care and Use of Laboratory published by the US National Institutes of Health (NIH Publication No. 85-23, revised 1996). Use of animals was approved by the Animal Use Subcommittee at the University of Western Ontario, Canada. C57BL/6 mice were purchased from Jackson Laboratory. A breeding program was carried out at the Lawson Health Research Institute animal care facility to produce offspring. Adult (3-4 months old) male mice weighing 21-26 g were studied.

Experimental Protocols.

Mice were randomly assigned to the following groups: saline (sham, n=5), lipopolysaccharide (LPS, n=7), and LPS plus recombinant human annexin A5 treatment group (n=6). LPS (4 mg/kg, i.p.) was employed to simulate sepsis. Mice were treated with 2 injections of recombinant human annexin A5 (5 μg/kg, i.v.) immediately and 2 hours after LPS administration. Four hours after LPS administration, mice were sacrificed and hearts were isolated. Cardiac function was measured using a Langendorff heart preparation. At the end of cardiac function measurements, hearts were stored in a −80° C. freezer for analysis of myocardial TNF expression.

Measurement of TNF mRNA by Real-Time RT-PCR.

Total RNA was isolated from LV myocardium with TRizol reagent (Invitrogen, Burlington, Ontario) as described previously [7, 8]. cDNA was synthesized using M-MLV reverse transcriptase and random primers (Invitrogen,). Real-time PCR was conducted using SYBR Green PCR Master Mix as per manufacturer's instructions (Abm, Vecouver, BC). The oligonucleotide primers for TNF were sense 5' CCG ATG GGT TGT ACC TTG TC 3' (SEQ ID NO. 1); and antisense, 5' GGG CTG GGT AGA GAA TGG AT 3' (SEQ ID NO. 2). 28S rRNA was used as a loading control using oligonucleotide primers for sense 5' TTG AAA ATC CGG GGG AGA G 3' (SEQ ID NO. 3) and antisense 5' ACA TTG TTC CAA CAT GCC AG 3' (SEQ ID NO. 4). Samples were amplified for 35 cycles using MJ Research Opticon Real-Time PCR machine. Levels of TNF mRNA relative to those of 28S rRNA were obtained similar to a previous report [9].

Measurement of TNF Protein Levels.

Left ventricle (LV) myocardial TNF protein levels were measured using a mouse TNF ELISA kit (Cedarlane Laboratory, Missisauga, Ontario) as described in previous reports [7, 10]. The LV myocardial tissues were homogenized in PBS. After centrifugation, the supernatant was collected for protein concentration and TNF ELISA. TNF measurements were standardized with protein concentrations of each sample and expressed as pg/mg proteins.

Isolated Mouse Heart Preparation.

After 4 hours of saline, LPS, or LPS plus Annexin A5 treatment, mice were sacrificed. Mouse hearts were isolated and perfused in a Langendorff system to measure cardiac function as previously described [10]. Briefly, hearts were perfused with Krebs-Henseleit buffer at 2 mL/min constant flow. The perfusion buffer was maintained at 37° C. and bubbled continuously with a mixture of 95% $O_2$ and 5% $CO_2$. A 6-0 silk suture was placed through the apex of the left ventricle and threaded through a lightweight rigid coupling rod, which was connected to a force-displacement transducer (FT03, Grass Instrument Co.). Contractile force and heart rate were measured by PowerLab Chart program (ADInstruments, Mountain View, Calif.). The heart work was calculated by multiplying the force (g) by the heart rate (beats/min) and normalized to heart weight.

Statistical Analysis.

All results are expressed as mean±SEM. One-way analysis of variance (ANOVA) followed by the Newman-Keul's post hoc test was used to detect differences between treatment groups. Statistical significance was assigned when a P value was less than 0.05.

Example 2

Effects of Annexin A5 on Cardiac Function in a Sepsis Model

Sepsis is a common clinical problem that occurs in 2-11% of all hospital or intensive care unit admissions [11, 12]. Despite tremendous research efforts over the last 20 years, sepsis remains the leading cause of death in intensive care units. Myocardial dysfunction is common in patients with severe sepsis and renders septic patients at high risk of developing multi-organ failure, which is associated with a high mortality [13]. Endotoxins or LPS are significant pathogens responsible for myocardial depression during sepsis [3, 4]. The inhibitory effect of LPS on cardiac function is mediated through the production of pro-inflammatory cytokines [14]. Among these cytokines, TNF-α has been proposed as one of the main factors for cardiac dysfunction during sepsis [4, 15]. Cardiomyocytes synthesize TNF-α after LPS challenge [15-17] and high levels of TNF-α produced within the myocardium contribute to the development of cardiac dysfunction [17].

To simulate severe sepsis in humans, a rodent model of endotoxemia induced by LPS is widely used as a tool to study sepsis [8, 10]. Treatment with LPS is associated with sepsis-like symptoms accompanied by hematological changes similar to septic patients [18]. Furthermore, cytokine expression including TNF-α is markedly increased in endotoxemia [8, 10]. Additionally, previous studies have shown that LPS induces significant cardiac dysfunction as demonstrated by decreased systolic and diastolic functions as well as decreased mean arterial pressure in mice [Xiang et al., Circulation; 2009:120:1065-1074]. Taken together, these studies suggest that endotoxemia is an excellent model for human sepsis.

FIG. 1 shows that Annexin A5 improves cardiac function in mice with endotoxemia. Mice were treated with LPS for 4 hours (4 mg/kg i.p., n=7) to induce endotoxemia resulting in cardiac dysfunction. Treatment with Annexin A5 (5 μg/kg i.v., n=6) significantly improved cardiac function compared to LPS alone. Saline treatment (100 μL, i.p) served as sham controls (n=4). Data are mean±SEM and analyzed by one-way ANOVA followed by Newman-Keul's test. *P<0.01 vs. Sham, #P<0.05 vs. LPS.

Four hours after saline, LPS, or LPS plus Annexin A5 treatment, animals were sacrificed and cardiac function was measured using a Langendorff heart preparation. Heart rate and contractile force were recorded. Heart work and rate of contraction (+dF/dtmax) and relaxation (−dF/dtmin) were analyzed. Results showed that rate of contraction and relaxation, contractile force and heart work were significantly decreased in LPS treated group compared to sham group (FIG. 1, *P<0.001). Treatment with recombinant human Annexin A5 significantly improved all four cardiac parameters compared to the LPS group (FIG. 1, #P<0.01).

Example 3

Effects of Annexin A5 on Myocardial TNF Expression

Figure 2:
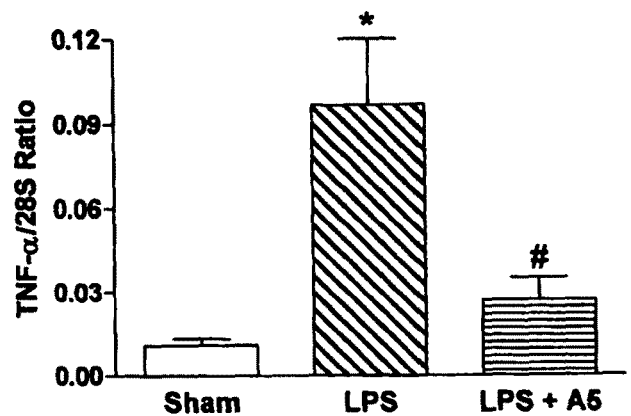
FIG. 2 shows an effect of Annexin A5 administration on myocardial TNF-α mRNA expression in mice with endotoxemia.

FIG. 2 shows an effect of Annexin A5 on myocardial TNF mRNA expression in endotoxemic mice. Mice were treated with LPS for 4 hours (4 mg/kg i.p., n=7) to induce endotoxemia and significant myocardial TNF mRNA expression compared to sham controls. Treatment with Annexin A5 (5 μg/kg i.v., n=6) significantly decreased myocardial TNF mRNA expression compared to LPS alone. Saline treatment (100 μL, i.p) served as sham controls (n=5). TNF mRNA levels were determined by real-time RT-PCR. Data are mean±SEM and analyzed by one-way ANOVA followed by Newman-Keul's test. *P<0.01 vs. Sham, #P<0.05 vs. LPS.

Figure 3:
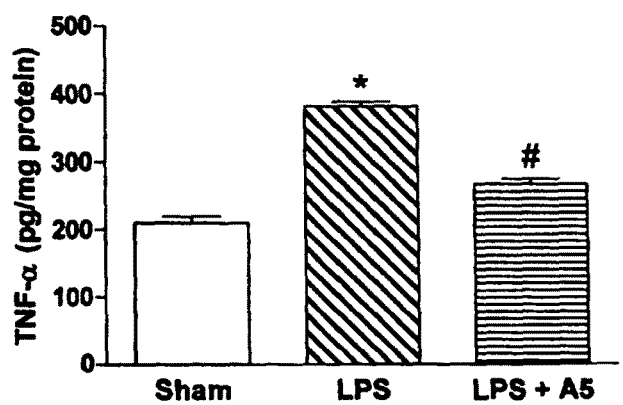
FIG. 3 shows an effect of Annexin A5 administration on myocardial TNF-α protein expression in mice with endotoxemia.

FIG. 3 shows an effect of Annexin A5 on myocardial TNF protein expression in endotoxemic mice. Mice were treated with LPS for 4 hours (4 mg/kg i.p., n=5) to induce endotoxemia and significant myocardial TNF protein expression compared to sham controls. Treatment with Annexin A5 (5 μg/kg i.v., n=6) significantly decreased myocardial TNF protein expression compared to LPS alone. Saline treatment (100 μL, i.p) served as sham controls (n=4). TNF protein levels were determined by ELISA. Data are mean±SEM and analyzed by one-way ANOVA followed by Newman-Keul's test. *$P<0.01$ vs. Sham, #$P<0.05$ vs. LPS.

Four hours after saline, LPS or LPS plus Annexin A5 treatment, myocardial TNF mRNA and protein expression was determined by real-time RT-PCR and ELISA, respectively. Both TNF mRNA and protein levels were significantly increased in the LV myocardium in LPS treated mice compared to saline treated sham controls ($P<0.01$). Treatment with Annexin A5 significantly decreased TNF expression induced by LPS ($P<0.05$).

In the present study, mouse endotoxemia, a mouse model of sepsis, was used to examine the effects of recombinant human Annexin A5 on cardiac function during an LPS challenge. To avoid the influences of cardiovascular reflex and loading conditions of the heart that may have on cardiac function measurements, an isolated Langendorff heart preparation was used. LPS induced cardiac dysfunction, which was partially restored by Annexin A5 treatment. The results demonstrate for the first time that Annexin A5 improves cardiac function during endotoxemia in mice. While Annexin A5 belongs to the same annexin superfamily as Annexin A1, they are separate proteins encoded by distinct genes [5]. In order to determine if Annexin A5 has anti-inflammatory effects, myocardial TNF-α expression was determined. The results provided in FIGS. 2 and 3 show that treatment with Annexin A5 significantly decreases both mRNA and protein levels of TNF-α in the LV myocardium during endotoxemia, suggesting an anti-inflammatory effect. As TNF-α production is a major contributor to cardiac dysfunction during sepsis, reduction of myocardial TNF-α expression represents an important mechanism by which Annexin A5 improves cardiac function in the endotexemia model.

Example 4

Experimental Protocols for Examples 5-10

Mice were randomly assigned to the following groups: saline (sham, n=15), recombinant human annexin A5 (n=11), lipopolysaccharide (LPS, n=16), and LPS plus recombinant human annexin A5 treatment group (n=17). LPS (4 mg/kg, i.p.) was administered to simulate sepsis. Mice were treated with 2 injections of recombinant human annexin A5 (5 μg/kg, i.v.) immediately and 2 hours after LPS administration. Four hours after LPS administration, mice were anesthetized with an IP injection of ketamine (50 mg/kg) and xylazine (12.5 mg/kg) mixture, and in vivo cardiac function was measured using a Millar pressure-conductance catheter. Some mice were sacrificed, blood was drawn and hearts were isolated. Ex vivo cardiac function was measured using a Langendorff heart preparation. At the end of cardiac function measurements, plasma and hearts were stored in a −80° C. freezer for further analysis.

Hemodynamic Measurements

After 4 hours of LPS and/or annexin A5 treatment, mice were anaesthetized with ketamine and xylazine. A Millar pressure-conductance catheter (Model SPR-839, Size 1.4F) was inserted into the right carotid artery and advanced into the LV. After stabilization for 10 minutes, the signal was recorded continuously using a PowerLab Chart program (ADInstruments, Mountain View, Calif.). Hemodynamic parameters were analysed by a cardiac pressure-volume analysis program (PVAN 3.2; Millar Instruments, TX) as previously described (Xiang et al. Circulation. 2009, 120:1065-1074).

Isolated Mouse Heart Preparation

After 4 hours of LPS and/or annexin A5 treatment, mice were sacrificed. Mouse hearts were isolated and perfused in a Langendorff system to measure cardiac function as previously described (Peng et al., Circulation. 2005; 111:1637-1644). Briefly, hearts were perfused with Krebs-Henseleit buffer at 2 mL/min constant flow. The perfusion buffer was maintained at 37° C. and bubbled continuously with a mixture of 95% $O_2$ and 5% $CO_2$. A 6-0 silk suture was placed through the apex of the left ventricle and threaded through a lightweight rigid coupling rod, which was connected to a force-displacement transducer (FT03, Grass Instrument Co.). Contractile force and heart rate were measured by PowerLab Chart program (ADInstruments, Mountain View, Calif.). The heart work was calculated by multiplying the force (g) by the heart rate (beats/min) and normalized to heart weight.

Measurement of TNF-α and Interleukin (IL)-1β mRNA by Real-Time RT-PCR

Total RNA was isolated from LV myocardium and cardiomyocytes with TRIzol reagent (Invitrogen, Burlington, Ontario) as described previously (Peng et al., Cardiovasc Res. 2003; 59:893-900: Geoghegan-Morphet et al., Cardiovasc Res. 2007; 75:408-416). cDNA was synthesized using M-MLV reverse transcriptase and random primers (Invitrogen, Burlington, Ontario). Real-time PCR was conducted using SYBR Green PCR Master Mix as per manufacturer's instructions (Abm, Vecouver, BC). The oligonucleotide primers for TNF-α were sense 5' CCG ATG GGT TGT ACC TTG TC 3' (SEQ ID NO. 1); and antisense, 5' GGG CTG GGT AGA GAA TGG AT 3' (SEQ ID NO. 2). The primers for IL-1β were sense 5' ACAAGGAGAACCAAGCAACGAC 3' (SEQ ID NO. 5) and antisense 5' GCTGATGTACCAGT-TGGGGAAC 3' (SEQ ID NO. 6). 28S rRNA was used as a loading control using oligonucleotide primers for sense 5' TTG AAA ATC CGG GGG AGA G 3' (SEQ ID NO. 3) and antisense 5' ACA TTG TTC CAA CAT GCC AG 3' (SEQ ID NO. 4). Samples were amplified for 35 cycles using MJ Research Opticon Real-Time PCR machine.

Measurement of TNF-α and IL-β Protein Levels

Myocardial and plasma TNF-α protein levels were measured using a mouse TNF-α ELISA kit (Cedarlane Laboratory, Missisauga, Ontario) as described in Applicant's previous reports[8,9]. The left ventricle (LV) myocardial tissues were homogenized in PBS. After centrifugation, the supernatant was collected for protein concentration and TNF-α ELISA. Myocardial TNF-α measurements were standardized with protein concentrations of each sample. Plasma IL-1β protein levels were determined using an ELISA kit from eBioscience Inc, CA.

Phosphorylation of p38 and ERK1/2 MAPK

Phosphorylated/total p38 and ERK1/2 protein levels in heart tissues were measured by western blot analysis. Briefly, 40 μg of protein was separated by sodium dodecyl sulfate-polyacrylamide gel electrophoresis. Proteins were then transferred to polyvinylidene difluoride membranes and blots were probed with antibodies against p38 (1:800, Cell Signaling, Danvers, Mass.), phosphorylated p38 (Thr 180/Tyr 182, 1:800, Cell Signaling), ERK1/2 (1:800, Cell Signaling), or phosphorylated ERK1/2 (Thr 202/Tyr 204, 1:800, Cell Signaling). Blots were probed with horseradish peroxidase-conjugated secondary antibodies (1:2000; BioRad, Hercules, Calif.) and detection was performed using an ECL chemiluminescence method.

Adult Cardiomyocyte Culture

Cardiomyocytes were isolated from the hearts of adult WT and nNOS$^{-/-}$ mice. Hearts were mounted on a Langendorff apparatus and perfused with digestion buffer containing 45 μg/mL of liberase blendzyme IV (Roche). Following digestion, cells were re-suspended and exposed to a series of sedimentation and resuspension steps in buffer containing increasing concentrations of Ca$^{2+}$ (12.5 μM-1.0 mM). The rod-shaped myocytes were then plated on laminin-coated 35-mm dishes at a density of 50 cells/mm$^2$ and cultured for 6 hours at 37° C. in a 2% $CO_2$ incubator. This was followed by 4 hours of LPS (2.5 μg/ml) treatment with or without annexin A5 (1.0 μg/ml).

Co-Immunoprecipitation

Co-immunoprecipitation of TLR4 and annexin A5 was performed using the Dynabead Protein G Immunprecipitation kits (Invitrogen, CA). Briefly, the magnetic dynabeads were suspended in an antibody-binding buffer with 20 μg of TLR4 antibody (Santa Cruz, Calif.) for 1 hour. Myocardial tissues were homogenized in NP40 cell lysis buffer and sonicated. Protein concentrations were measured using a Lowry protein assay (Bio-Rad, Mississauga, ON). Concentrations were measured to allow for equal loading of 1 mg protein per tube. 500 ng of human recombinant annexin A5 (Biovision, CA) was added to the tissue samples and incubated with the TLR4-coated beads for 2 hours. The samples were eluted from the dynabeads and equally loaded on a 12% polyacrylamide gel. Western blotting was performed for annexin A5 detection using anti-annexin A5 antibody (1:2000, Biovision, CA). The membrane was stripped and reprobed for TLR4 using anti-TLR4 antibody (1:2000, Santa Cruz, Calif.).

Statistical Analysis

All results are expressed as mean±SEM. Two-way analysis of variance (ANOVA) followed by unpaired Student's t test with Bonferroni corrections was performed to detect differences between treatment groups. Statistical significance was assigned when a P value was less than 0.05.

Example 5

Effects of Annexin A5 on Cardiac Function In Vivo

Figure 4:
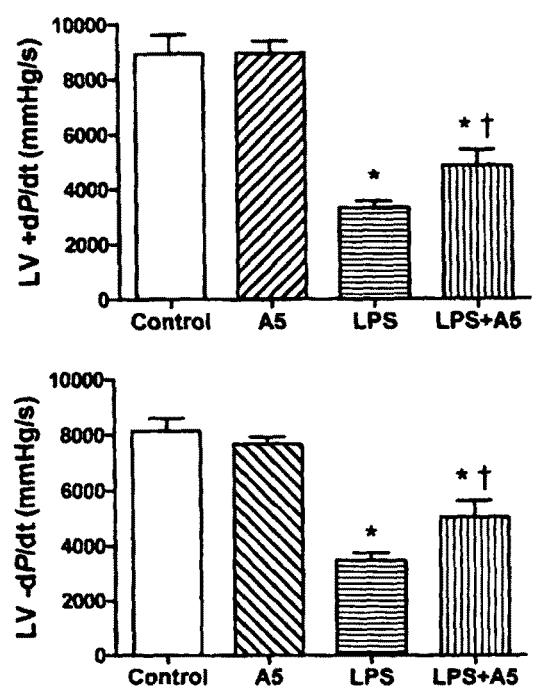
FIG. 4 confirms the experiment of FIG. 1 in that Annexin A5 (A5) improves in vivo cardiac function in mice with endotoxemia. Mice were treated with saline (control, 100 μL, i.p), A5 (5 μg/kg i.v.), LPS (4 mg/kg i.p.) or LPS plus A5 for 4 hours. A5 treatment significantly increased LV +dP/dt and −dP/dt in mice with endotoxemia. Data are mean±SEM and analyzed by two-way ANOVA followed by unpaired Student's t-test with Bonferroni corrections. *$P<0.01$ vs. control; †$P<0.05$ vs. LPS; n=9-11 per group.

Four hours after saline, annexin A5, LPS, or LPS plus annexin A5 treatment, mice were anesthetized and cardiac function was measured using a Millar pressure-conductance catheter. Hemodynamic parameters obtained include mean artery pressure (MAP), heart rate, left ventricle ejection fraction (LVEF), cardiac output, derivatives of left ventricular pressures (LV dP/dt$_{max}$ and dP/dt$_{min}$), pressure at maximal dP/dt (P@dP/dt$_{max}$), LV end systolic pressure (LVESP), LV end diastolic pressure (LVEDP), LV end diastolic volume (LVEDV), time constant of isovolumic relaxation (Tau) and maximal power (Table 2, FIG. 4). Following LPS treatment, MAP, LVEF, LV +dP/dt$_{max}$ and −dP/dt$_{min}$, P@dP/dt$_{max}$, LVESP, LVEDP and maximal power were significantly decreased (P<0.01) while LVEDV as significantly increased (P<0.01). Treatment of annexin A5 significantly increased LVESP and P@dP/dt$_{max}$ in endotoxemic mice (P<0.05, Table 2). Importantly, LV +dP/dt$_{max}$ and −dP/dt$_{min}$ were significantly increased in LPS with annexin A5 treatment compared to the LPS group (P<0.05, FIG. 4).

Example 6

Effects of Annexin A5 on Cardiac Function Ex Vivo

Figure 5:
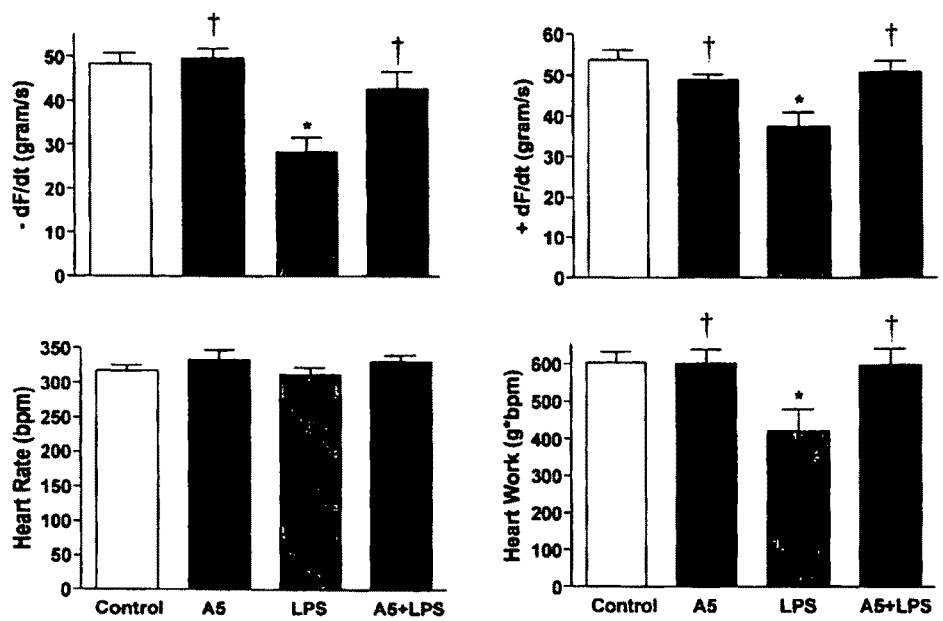
FIG. 5 shows Annexin A5 (A5) improves ex vivo cardiac function in mice with endotoxemia. Mice were treated with saline (control, 100 μL, i.p), A5 (5 μg/kg i.v.), LPS (4 mg/kg i.p.) or LPS plus A5 for 4 hours. A5 treatment significantly increased +dF/dt, −dF/dt and heart work in mice with endotoxemia. Data are mean±SEM and analyzed by two-way ANOVA followed by unpaired Student's t-test with Bonferroni corrections. *$P<0.01$ vs. control; †$P<0.05$ vs. LPS; n=4-7 per group.
Figure 6:
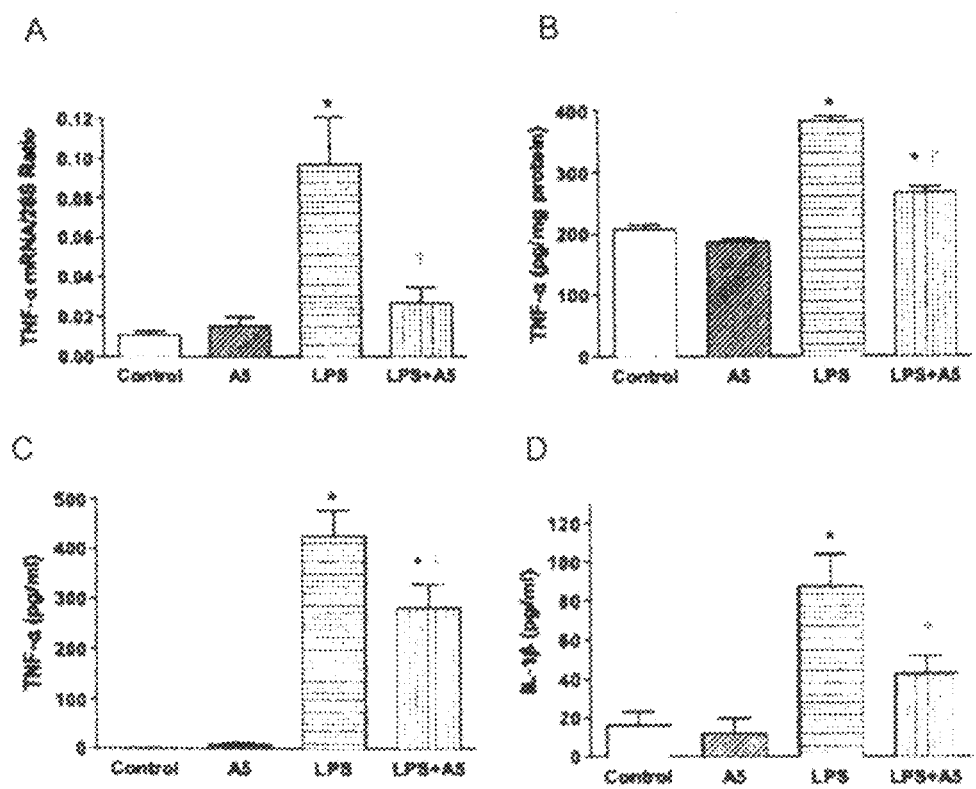
FIGS. 6A-D show the effects of annexin A5 (A5) on TNF-α and IL-1β production in endotoxemic mice. Mice were treated with saline (control, 100 μL, i.p), A5 (5 μg/kg i.v.), LPS (4 mg/kg i.p.) or LPS plus A5 for 4 hours. A and B. Treatment with A5 (5 μg/kg, i.v.) significantly decreased myocardial TNF-α mRNA and protein expression during endotoxemia. C and D. Plasma levels of TNF-α and IL-β were significantly decreased by A5 treatment during endotoxemia. Data are mean±SEM and analyzed by two-way ANOVA followed by unpaired Student's t-test with Bonferroni corrections. *$P<0.01$ vs. control; †$P<0.05$ vs. LPS; n=8-12 per group.

Four hours after saline, annexin A5, LPS, or LPS plus annexin A5 treatment, animals were sacrificed and cardiac function was measured using a Langendorff heart preparation. Heart rate and contractile force were recorded. Heart work and rate of contraction (+dF/dt$_{max}$) and relaxation (−dF/dt$_{min}$) were analyzed. Results showed that rate of contraction and relaxation, contractile force and heart work were significantly decreased in LPS treated group compared to sham group (FIG. 5, P<0.001). Treatment with recombinant human annexin A5 significantly improved all four cardiac parameters compared to the LPS group (FIG. 6, P<0.01).

Example 7

Effects of Annexin A5 on Myocardial and Plasma TNF-α Levels

Four hours after saline, annexin A5, LPS or LPS plus annexin A5 treatment, myocardial TNF mRNA and protein expression was determined by real-time RT-PCR and ELISA, respectively. Both TNF-α mRNA and protein levels were significantly increased in the LV myocardium in LPS treated mice compared to saline treated sham controls (P<0.01, FIGS. 6A and 6B). Treatment with annexin A5 significantly decreased TNF-α expression induced by LPS (P<0.05, FIGS. 6A and 6B). Similarly, plasma levels of TNF-α and IL-1β were significantly increased in LPS treated mice (P<0.01), which were significantly decreased by annexin A5 treatment (P<0.05, FIGS. 6C and 6D).

Example 8

Effects of Annexin A5 on Myocardial p38 and ERK1/2 Phosphorylation

Figure 7:
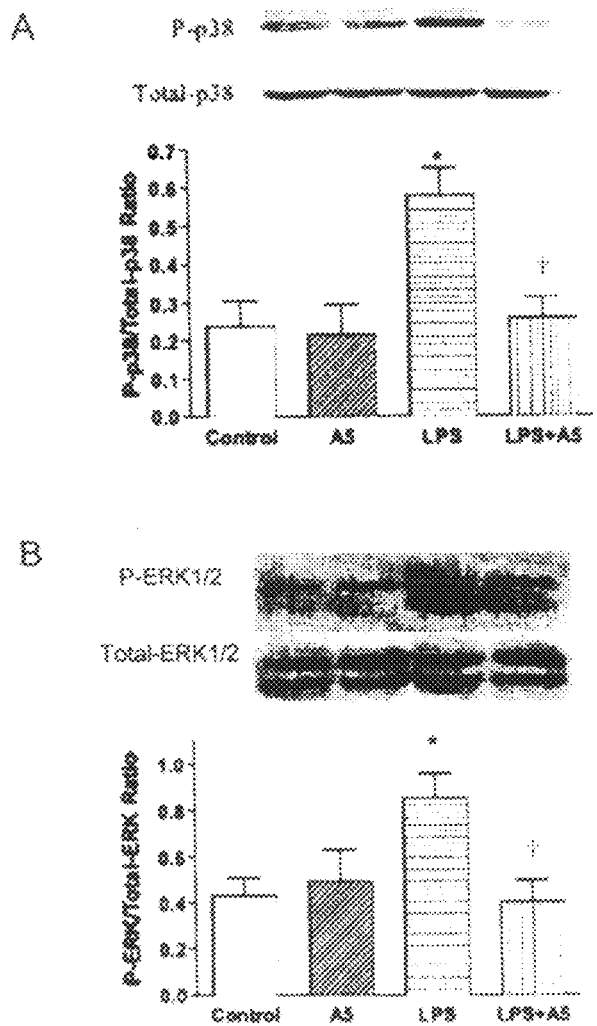
FIGS. 7A and B show that Annexin A5 (A5) decreases myocardial p38 and ERK1/2 MAPK phosphorylation during endotoxemia. Mice were treated with saline (control, 100 μL i.p), A5 (5 μg/kg i.v.), LPS (4 mg/kg i.p.) or LPS plus A5 for 30 minutes. A. Myocardial p38 phosphorylation. B. ERK1/2 phosphorylation. Phosphorylation of p38 and ERK1/2 was determined by western blot analysis. Data are mean±SEM and analyzed by two-way ANOVA followed by unpaired Student's t-test with Bonferroni corrections. *$P<0.05$ vs. Control; †$P<0.05$ vs. LPS; n=4-6 per group.

We have demonstrated that activation of p38 and ERK1/2 MAPK by LPS results in myocardial TNF-α expression. Since p38 and ERK1/2 play an important role in LPS-induced TNF-α expression, effects of annexin A5 on myocardial p38 and ERK1/2 phosphorylation were studied using western blot analysis. Thirty minutes after LPS (4 mg/kg, IP) treatment, myocardial p38 and ERK1/2 phosphorylation was significantly increased (P<0.05, FIG. 4). Treatment of annexin A5 together with LPS restored p38 and ERK1/2 phosphorylation to the control levels (P<0.05, FIG. 7).

Example 9

Effects of Annexin A5 on TNF-α and IL-1β Expression in Cardiomyocytes

Figure 8:
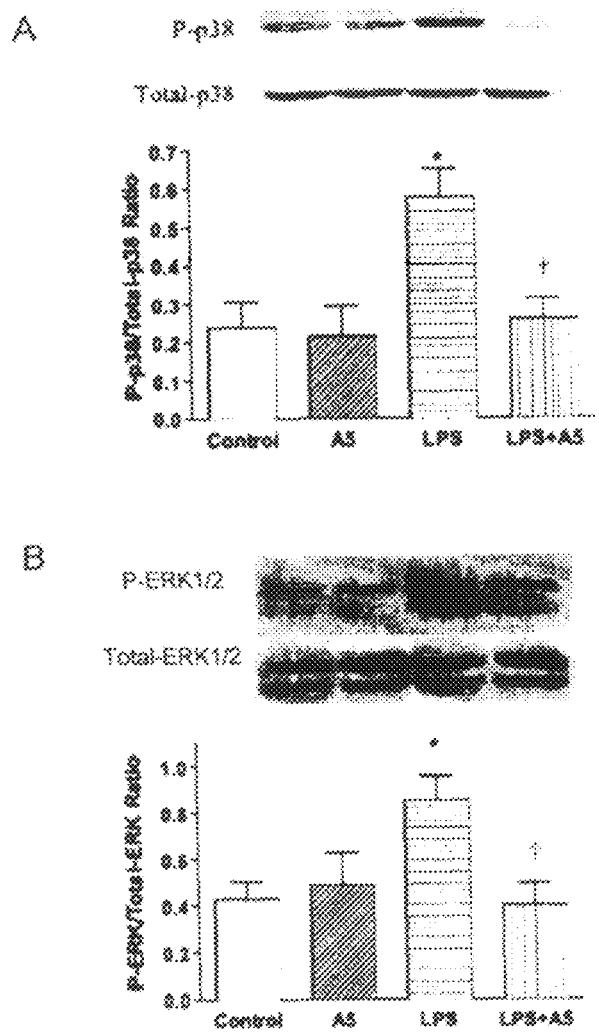
FIGS. 8A and B show that Annexin A5 (A5) inhibits TNF-α and IL-1β mRNA expression in adult cardiomyocytes. Adult cardiomyocytes were cultured on 35 mm dishes. Cells were treated with LPS (2.5 μg/ml) in the presence or absence of A5 (1 μg/ml) for 6 hours. TNF-α (A) and IL-β (B) mRNA levels were determined by real time RT-PCR analysis with 28S as a loading control. Data are mean±SEM and analyzed by two-way ANOVA followed by unpaired Student's t-test with Bonferroni corrections. *$P<0.01$ vs. control, †$P<0.05$ vs. LPS; n=3-4 independent experiments per group.

In order to determine the direct effects of annexin A5 on TNF-α and IL-1β expression in cardiomyocytes, adult cardiomyocytes were isolated and cultured. Consistent with the in vivo data reported above, LPS significantly increased TNF-α and IL-1β mRNA levels measured by real-time RT-PCR in the cultured adult cardiomyocytes and the response was abrogated by annexin A5 treatment (P<0.05, FIGS. 8A and 8B).

Example 10

Interaction Between Annexin A5 and TLR4 Receptors

Figure 9:
FIG. 9 shows that Annexin A5 interacts with TLR4 in myocardial tissue as determined by co-immunoprecipitation analysis. Myocardial tissue was homogenized and incubated with 0.5 μg annexin A5. TLR4 protein was pulled down using magnetic beads coated with anti-TLR4 antibody. This was followed by a Western blot analysis for annexin A5. Lane 1, a control myocardial sample from mice treated with saline. Lane 2, myocardial sample from LPS treated mice (4 mg/kg, i.p. for 4 hours). Lane 3, recombinant annexin A5 positive control. The blot shown is a representative from 3 experiments.

To further determine the mechanism by which annexin A5 inhibits LPS-induced TLR4 signaling, interaction between annexin A5 and TLR4 receptors was studied using co-immunoprecipitation. Myocardial tissues from saline and LPS-treated mice were homogenized and incubated with annexin A5. Magnetic dynabeads were coated with anti-TLR4 antibody to pull down TLR4 receptors and blot for annexin A5. Recombinant human annexin A5 was used as a positive control. Data showed that an annexin A5 specific band in myocardial samples from both saline and LPS-treated mice, indicating an interaction between annexin A5 and TLR4 receptors (FIG. 9).

The mouse model of endotoxemia demonstrated human annexin A5 effects on cardiac function during an LPS challenge. In vivo cardiac function was determined using a Millar pressure-conductance catheter. The data showed that cardiac dysfunction induced by LPS was significantly improved after annexin A5 treatment. To avoid the influences of cardiovascular reflex and loading conditions of the heart that may have on cardiac function measurements, an isolated Langendorff heart preparation was used. In agreement with the in vivo data, LPS-induced cardiac dysfunction was partially restored by annexin A5 treatment. Thus, these results demonstrated herein for the first time that annexin A5 improves cardiac function during endotoxemia in mice.

The results also demonstrate that treatment with annexin A5 significantly decreased both mRNA and protein levels of TNF-α in the LV myocardium during endotoxemia. In addition to decreased myocardial TNF-α expression, plasma levels of TNF-α and IL-1β were also decreased by annexin A5 treatment in the endotoxemic mice. Furthermore, annexin A5 treatment inhibited TNF-α and IL-β expression in the cultured adult cardiomyocytes. These data demonstrate that annexin A5 has an anti-inflammatory effect. Myocardial p38 and ERK1/2 phosphorylation was also demonstrated to be increased after LPS treatment. The increased p38 and ERK1/2 phosphorylation was completely abrogated by the treatment of annexin A5, demonstrating that the annexin A5 interferes with the TLR4/MAPK signaling pathway. Annexin A5 may interact with the leucine rich repeats of the TLR4 receptor and inhibit LPS-induced signaling. Co-immunoprecipitation to identify potential interaction between annexin A5 and TLR4 was done and the data showed that annexin A5 was co-immunoprecipitated with TLR4, suggesting an interaction between annexin A5 and TLR4 receptors. Since binding to leucine rich repeats by annexin A5 has been shown to inhibit receptor function, it is likely that annexin A5 inhibits LPS-induced TLR4/MAPK signaling through its interaction with the TLR4 receptors.

In summary, the data presented herein shows a novel effect of annexin A5 in a mouse model of endotoxemia. Treatment with annexin A5 decreases myocardial TNF-α expression and improves cardiac function during endotoxemia. These beneficial effects of annexin A5 are achieved through inhibition of TLR4/MAPK signaling via its interaction with the TLR4 receptors. Thus annexin A5 has significant therapeutic use in the treatment of sepsis.

TABLE 1

Shows the mRNA and amino acid sequences for human Annexin A5.
The mRNA coding sequence is shown in bold.

mRNA Sequence for Human Annexin A5: (SEQ ID NO. 7)

```
   1 gttgcttgga tcagtctagg tgcagctgcc ggatccttca gcgtctgcat ctcggcgtcg
  61 ccccgcgtac cgtcgcccgg ctctccgccg ctctcccggg gtttcggggc actttgggtcc
 121 cacagtctgg tcctgcttca ccttcccctg acctgagtag tcgccatggc acaggttctc
 181 agaggcactg tgactgactt ccctggattt gatgagcggg ctgatgcaga aactcttcgg
 241 aaggctatga aaggcttggg cacagatgag gagagcatcc tgactctgtt gacatcccga
 301 agtaatgctc agcgccagga aatctctgca gcttttaaga ctctgtttgg cagggatctt
 361 ctggatgacc tgaaatcaga actaactgga aaatttgaaa aattaattgt ggctctgatg
 421 aaaccctctc ggctttatga tgcttatgaa ctgaaacatg ccttgaaggg agctggaaca
 481 aatgaaaaag tactgacaga aattattgct tcaaggacac ctgaagaact gagagccatc
 541 aaacaagttt atgaagaaga atatggctca agcctggaag atgacgtggt gggggacact
 601 tcagggtact accagcggat gttggtggtt ctccttcagg ctaacagaga ccctgatgct
 661 ggaattgatg aagctcaagt tgaacaagat gctcaggctt tatttcaggc tggagaactt
 721 aaatggggga cagatgaaga aaagtttatc accatctttg gaacacgaag tgtgtctcat
 781 ttgagaaagg tgtttgacaa gtacatgact atatcaggat ttcaaattga ggaaaccatt
 841 gaccgcgaga cttctggcaa tttagagcaa ctactccttg ctgttgtgaa atctattcga
 901 agtatacctg cctaccttgc agagaccctc tattatgcta tgaagggagc tgggacagat
 961 gatcatacce tcatcagagt catggtttcc aggagtgaga ttgatctgtt taacatcagg
1021 aaggagttta ggaagaattt tgccacctct ctttattcca tgattaaggg agatacatct
1081 ggggactata agaaagctct tctgctgctc tgtggagaag atgactaacg tgtcacgggg
1141 aagagctccc tgctgtgtgc ctgcaccacc ccactgcctt ccttcagcac ctttagctgc
1201 atttgtatgc cagtgcttaa cacattgcct tattcatact agcatgctca tgaccaacac
1261 atacacgtca tagaagaaaa tagtggtgct tctttctgat ctctagtgga gatctctttg
1321 actgctgtag tactaaagtg tacttaatgt tactaagttt aatgcctggc cattttccat
1381 ttatatatat tttttaagag gctagagtgc ttttagcctt ttttaaaaac tccatttata
1441 ttacatttgt aaccatgata ctttaatcag aagcttagcc ttgaaattgt gaactcttgg
1501 aaatgttatt agtgaagttc gcaactaaac taaacctgta aaattatgat gattgtattc
1561 aaaagattaa tgaaaaataa acatttctgt ccccctgaaa aaaaaaaaaa aaaaaaaaaa
1621 aaaa
```

Amino Acid Sequence for Human Annexin A5: (SEQ ID NO. 8)

```
   1 maqvlrgtvt dfpgfderad aetlrkamkg lgtdeesilt lltsrsnaqr qeisaafktl
  61 fgrdllddlk seltgkfekl ivalmkpsrl ydayelkhal kgagtnekvl teiiasrtpe
 121 elraikqvye eeygssledd vvgdtsgyyq rmlvvllqan rdpdagidea qveqdagalf
 181 qagelkwgtd eekfitifgt rsvshlrkvf dkymtisgfq ieetidrets gnleqlllav
 241 vksirsipay laetlyyamk gagtddhtli rvmvsrseid lfnirkefrk nfatslysmi
 301 kgdtsgdykk allllcgedd
```

TABLE 2

In vivo hemodynamic measurements in mice with endotoxemia

| Parameters | Saline | A5 | LPS | LPS + A5 |
|---|---|---|---|---|
| n | 10 | 11 | 9 | 11 |
| Heart rate, beats/min | 412 ± 23 | 395 ± 9 | 473 ± 17 | 489 ± 17 |
| MAP, mmHg | 86 ± 3 | 83 ± 5 | 44 ± 3** | 52 ± 4** |
| LVEF, % | 63 ± 6 | 67 ± 7 | 13 ± 3** | 17 ± 2** |
| Cardiac output, μL/min | 5188 ± 834 | 3698 ± 558 | 3511 ± 835 | 4664 ± 810 |
| P@dP/dt$_{max}$, mmHg | 64 ± 2 | 64 ± 4 | 31 ± 2** | 40 ± 3**† |
| LVESP, mmHg | 102 ± 5 | 95 ± 8 | 66 ± 2** | 77 ± 4**† |
| LVEDP, mmHg | 6.9 ± 0.9 | 6.5 ± 0.7 | 3.6 ± 0.2** | 4.9 ± 0.5** |
| LVEDV, μL | 20 ± 4 | 14 ± 3 | 50 ± 4** | 61 ± 7** |
| Tau, ms | 7.9 ± 0.3 | 8.1 ± 0.5 | 9.9 ± 0.5 | 8.5 ± 0.5 |
| Maximal Power, mWatts | 6.1 ± 1.1 | 4.4 ± 0.8 | 2.0 ± 0.6** | 3.8 ± 0.8 |

Data are mean ± SEM and analyzed by two-way ANOVA followed by unpaired Student's t-test with Bonferroni corrections.
**$P < 0.01$ vs. saline,
†$P < 0.05$ vs. LPS.
MAP, mean artery pressure;
SW, stroke work;
P@dP/dt$_{max}$, LV pressure at maximal dP/dt;
LVESP, LV end systolic pressure;
LVEDP, LV end diastolic pressure;
LVEDV, LV end diastolic volume;
Tau, time constant of isovolumic relaxation.

REFERENCES

1. Angus D C, Linde-Zwirble W T, Lidicker J, Clermont G, Carcillo J, Pinsky M R. Epidemiology of severe sepsis in the United States: analysis of incidence, outcome, and associated costs of care. Crit Care Med 2001; 29:1303-1310.
2. Parrillo J E, Parker M M, Natanson C, Suffredini A F, Danner R L, Cunnion R E, Ognibene F P. Septic shock in humans. Advances in the understanding of pathogenesis, cardiovascular dysfunction, and therapy. Ann Intern Med 1990; 113:227-242.
3. Suffredini A F, Fromm R E, Parker M M, Brenner M, Kovacs J A, Wesley R A, Parrillo J E. The cardiovascular response of normal humans to the administration of endotoxin. N Engl J Med 1989; 321:280-287.
4. Natanson C, Eichenholz P W, Danner R L, Eichacker P Q, Hoffman W D, Kuo G C, Banks S M et al. Endotoxin and tumor necrosis factor challenges in dogs simulate the cardiovascular profile of human septic shock. J Exp Med 1989; 169:823-832.
5. Gerke V, Moss S E. Annexins: from structure to function. Physiol Rev 2002; 82:331-371.
6. Reutelingsperger C P, van Heerde W L. Annexin V, the regulator of phosphatidylserine-catalyzed inflammation and coagulation during apoptosis. Cell Mol Life Sci 1997; 53:527-532.
7. Peng T, Lu X, Lei M, Moe G W, Feng a Inhibition of p38 MAPK decreases myocardial TNF-alpha expression and improves myocardial function and survival during acute endotoxemia in mice. Cardiovasc Res 2003; 59:893-900.
8. Geoghegan-Morphet N, Burger D, Lu X, Sathish V, Peng T, Sims S M, Feng Q, Role of neuronal nitric oxide synthase in lipopolysaccharide-induced tumor necrosis factor-alpha expression in neonatal mouse cardiomyocytes. Cardiovasc Res 2007; 75:408-416.
9. Hammoud L, Xiang F, Lu X, Brunner F, Leco K, Feng Q. Endothelial nitric oxide synthase promotes neonatal cardiomyocyte proliferation by inhibiting tissue inhibitor of metalloproteinase-3 expression. Cardiovasc Res 2007; 75:359-368.
10. Peng T, Lu X, Feng Q. Pivotal role of gp91phox-containing NADH oxidase in lipopolysaccharide-induced tumor necrosis factor-alpha expression and myocardial depression. Circulation 2005; 111:1637-1644.
11. Angus D C, Wax R S. Epidemiology of sepsis: an update. Crit Care Med 2001; 29:S109-116.
12. Martin G S, Mannino D M, Eaton S, Moss M. The epidemiology of sepsis in the United States from 1979 through 2000. N Engl J Med 2003; 348:1546-1554.
13. Court O, Kumar A, Parrillo J E. Clinical review: Myocardial depression in sepsis and septic shock. Crit Care 2002; 6:500-508.
14. Parrillo J E, Burch C, Shelhammer J H, Parker M M, Natanson C, Schuette W. A circulating myocardial depressant substance in humans with septic shock. J Clin Invest 1985; 76:1539-1553.
15. Peng T, Lu X, Lei M, Feng Q. Endothelial nitric-oxide synthase enhances lipopolysaccharide-stimulated tumor necrosis factor-alpha expression via cAMP-mediated p38 MAPK pathway in cardiomyocytes. J Biol Chem 2003; 278:8099-8105.
16. Kapadia S, Lee J, Torre-Amione G, Birdsall H H, Ma T S, Mann D L. Tumor necrosis factor-alpha gene and protein expression in adult feline myocardium after endotoxin administration. J Clin Invest 1995; 96:1042-1052.
17. Grandel U, Fink L, Blum A, Heep M, Buerke M, Kraemer H J, Mayer K et al. Endotoxin-induced myocardial tumor necrosis factor-alpha synthesis depresses contractility of isolated rat hearts: evidence for a role of sphingosine and cyclooxygenase-2-derived thromboxane production. Circulation 2002; 102:2758-2764.
18. Remick D G, Newcomb D E, Bolgos G L, Call D R. Comparison of the mortality and inflammatory response of two models of sepsis: lipopolysaccharide vs. cecal ligation and puncture. Shock 2000; 13:110-116.

19. Damazo A S, Yona S, D'Acquisto F, Flower R J, Oliani S M, Perretti M. Critical protective role for annexin 1 gene expression in the endotoxemic murine microcirculation. Am J Pathol 2005; 166:1607-1617.
21. Peng T, Lu X, Zhang T, Feng Q, JNK1/c-fos inhibits cardiomyocyte TNF-a expression via a negative crosstalk with ERK and p38 MAPK in endotoxemia. *Cardiovasc Res.* 2009; 81:733-741.
22. Markoff A, Bogdanova N, Knop M, Ruffer C, Kenis H, Lux P, Reutelingsperger C, Todorov V, Dworniczak B, Horst J, Gerke V. Annexin A5 interacts with polycystin-1 and interferes with the polycystin-1 stimulated recruitment of E-cadherin into adherens junctions. *J Mol Biol.* 2007; 369:954-966.

The above-described embodiments are intended to be examples and alterations and modifications may be effected thereto, by those of skill in the art, without departing from the scope of the invention which is defined by the claims appended hereto.

What is claimed is:

1. A method for treatment of sepsis in a subject not having a blood coagulation disorder comprising administering an effective amount of Annexin A5 to the subject, wherein the Annexin A5 interacts with TLR4 receptors.

2. The method of claim 1, wherein the amount of Annexin A5 is effective to inhibit a proinflammatory cytokine selected from the group consisting of TNF-α and IL-1β.

3. The method of claim 1, wherein the Annexin A5 is selected from the group consisting of an Annexin A5 polypeptide, an Annexin A5 nucleic acid and a recombinant cell comprising Annexin A5.

4. The method of claim 1, wherein the subject is a mammal selected from the group consisting of mouse, pig, dog, rat, and human.

5. The method of claim 1, wherein the Annexin A5 is a full-length naturally occurring polypeptide.

6. The method of claim 1, wherein the sepsis is characterized by at least two of the following: tachycardia; hypothermia; fever; tachypnea; hypocapnia; leukopenia; leukocytosis; and bandemia and wherein infection is suspected or proven.

7. The method of claim 6, wherein the sepsis is further characterized by systemic hypoperfusion.

8. The method of claim 6, wherein the sepsis is further characterized by hypotension after fluid resuscitation.

9. A method for treatment of sepsis in a subject not having a blood coagulation disorder to reduce occurrence of disseminated intravascular coagulation (DIC), the method comprising administering an effective amount of Annexin A5 to the subject, wherein the Annexin A5 interacts with TLR4 receptors, and wherein the Annexin A5 does not treat a blood coagulation disorder.

10. The method of claim 9, wherein the amount of Annexin A5 is effective to inhibit a proinflammatory cytokine selected from the group consisting of TNF-α and IL-1β.

11. The method of claim 9, wherein the Annexin A5 is selected from the group consisting of an Annexin A5 polypeptide, an Annexin A5 nucleic acid and a recombinant cell comprising Annexin A5.

12. The method of claim 9, wherein the subject is a mammal selected from the group consisting of mouse, pig, dog, rat, and human.

13. The method of claim 9, wherein the Annexin A5 is a full-length naturally occurring polypeptide.

14. The method of claim 9, wherein the sepsis is characterized by at least two of the following: tachycardia; hypothermia; fever; tachypnea; hypocapnia; leukopenia; leukocytosis; and bandemia and wherein infection is suspected or proven.

15. The method of claim 14, wherein the sepsis is further characterized by systemic hypoperfusion.

16. The method of claim 14, wherein the sepsis is further characterized by hypotension after fluid resuscitation.

17. The method of claim 1, wherein the Annexin A5 is administered in an amount of less than 0.04 mg/kg/day.

18. The method of claim 1, wherein the Annexin A5 is administered in an amount of less than 0.03 mg/kg/day.

19. The method of claim 1, wherein the Annexin A5 is administered in an amount of less than 0.02 mg/kg/day.

20. The method of claim 1, wherein the Annexin A5 is administered in an amount of less than 0.01 mg/kg/day.

21. The method of claim 1, wherein the Annexin A5 is administered in an amount of from about 1 to 10 mg/kg/day.

22. The method of claim 1, wherein the Annexin A5 is administered in an amount of 1.0 mg/kg/day.

23. The method of claim 1, wherein the Annexin A5 is administered in an amount of more than 20 mg/kg/day.

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Artificial sequence
<220> FEATURE:
<223> OTHER INFORMATION: Synthetic primer

<400> SEQUENCE: 1
ccgatgggtt gtaccttgtc                                              20

<210> SEQ ID NO 2
<211> LENGTH: 20
<212> TYPE: DNA
<213> ORGANISM: Artificial sequence
<220> FEATURE:
<223> OTHER INFORMATION: Synthetic primer

<400> SEQUENCE: 2
gggctgggta gagaatggat                                              20

<210> SEQ ID NO 3
<211> LENGTH: 19
<212> TYPE: DNA
<213> ORGANISM: Artificial sequence
<220> FEATURE:
<223> OTHER INFORMATION: Synthetic primer

<400> SEQUENCE: 3
ttgaaaatcc gggggagag                                               19

<210> SEQ ID NO 4
<211> LENGTH: 20
<212> TYPE: DNA
<213> ORGANISM: Artificial sequence
<220> FEATURE:
<223> OTHER INFORMATION: Synthetic primer

<400> SEQUENCE: 4
acattgttcc aacatgccag                                              20

<210> SEQ ID NO 5
<211> LENGTH: 22
<212> TYPE: DNA
<213> ORGANISM: Artificial sequence
<220> FEATURE:
<223> OTHER INFORMATION: Synthetic primer

<400> SEQUENCE: 5
acaaggagaa ccaagcaacg ac                                           22

-continued

```
<210> SEQ ID NO 6
<211> LENGTH: 22
<212> TYPE: DNA
<213> ORGANISM: Artificial sequence
<220> FEATURE:
<223> OTHER INFORMATION: Synthetic primer

<400> SEQUENCE: 6
gctgatgtac cagttgggga ac                                              22

<210> SEQ ID NO 7
<211> LENGTH: 1624
<212> TYPE: DNA
<213> ORGANISM: Artificial Sequence
<220> FEATURE:
<223> OTHER INFORMATION: Human Annexin A5

<400> SEQUENCE: 7
gttgcttgga tcagtctagg tgcagctgcc ggatccttca gcgtctgcat ctcggcgtcg      60
ccccgcgtac cgtcgcccgg ctctccgccg ctctcccggg gtttcggggc acttgggtcc    120
cacagtctgg tcctgcttca ccttcccctg acctgagtag tcgccatggc acaggttctc    180
agaggcactg tgactgactt ccctggatt t gatgagcggg ctgatgcaga aactcttcgg    240
aaggctatga aaggcttggg cacagatgag gagagsatcc tgactctgtt gacatcccga    300
agtaatgcts agcgccagga aatctctgca gcttttaaga ctctgtttgg cagggatctt    360
ctggatgacc tgaaatcaga actaactgga aaatttgaaa attaattgt ggstctgatg    420 aaaccctctc ggctttatga tgcttatgaa ctgaaacatg ccttgaaggg agctggaaca    480
aatgaaaaag tactgacaga aattattgct tcaaggacac ctgaagaact gagagccatc    540
aaacaagttt atgaagaaga atatggctca agcctggaag atgacgtggt ggggacact    600 tcagggtact accagcggat gttggtggtt ctccttcagg ctaacagaga ccctgatgct    660
ggaattgatg aagctcaagt tgaacaagat gctcaggctt atttcaggc tggagaactt    720 aaatggggga cagatgaaga aaagtttatc accatctttg gaacacgaag tgtgtctcat    780
ttgagaaagg tgtttgacaa gtacatgact atatcaggat ttcaaattga ggaaaccatt    840
gaccgcgaga sttctggcaa tttagagcaa ctactccttg ctgttgtgaa atctattcga    900 agtataccetg cctaccttge agagaccctc tattatgcta tgaagggagc tgggacagat    960
gatcataccc tcatcagagt catggtttcc aggagtgaga ttgatctgtt taacatcagg   1020
aaggagttta ggaagaattt tgccacctct ctttattcca tgattaaggg agatacatct   1080
ggggastata agaaagctct tctgctgctc tgtggagaag atgastaacg tgtcacgggg   1140
aagagctccc tgctgtgtgc ctgcaccacc ccactgcctt ccttcagcac ctttagctgc   1200
atttgtatgc cagtgcttaa cacattgcct tattcatact agcatgctca tgaccaacac   1260
atacacgtca tagaagaaaa tagtggtgct tctttctgat ctctagtgga gatctctttg   1320
actgctgtag tactaaagtg tacttaatgt tactaagttt aatgcctggc cattttccat   1380
ttatatatat tttttaagag gctagagtgc tttttagcctt ttttaaaaac tccatttata   1440
ttacatttgt aaccatgata ctttaatcag aagcttagcc ttgaaattgt gaactcttgg   1500
aaatgttatt agtgaagttc gcaactaaac taaacctgta aaattatgat gattgtattc   1560
aaaagattaa tgaaaaataa acatttctgt cccccctgaaa aaaaaaaaaa aaaaaaaa     1620 aaaa                                                                 1624
```

```
<210> SEQ ID NO 8
<211> LENGTH: 320
<212> TYPE: PRT
<213> ORGANISM: Artificial Sequence
<220> FEATURE:
<223> OTHER INFORMATION: Human Annexin A5

<400> SEQUENCE: 8

Met Ala Gln Val Leu Arg Gly Thr Val Thr Asp Phe Pro Gly Phe Asp
1               5                   10                  15

Glu Arg Ala Asp Ala Glu Thr Leu Arg Lys Ala Met Lys Gly Leu Gly
                20                  25                  30

Thr Asp Glu Glu Ser Ile Leu Thr Leu Leu Thr Ser Arg Ser Asn Ala
            35                  40                  45

Gln Arg Gln Glu Ile Ser Ala Ala Phe Lys Thr Leu Phe Gly Arg Asp
        50                  55                  60

Leu Leu Asp Asp Leu Lys Ser Glu Leu Thr Gly Lys Phe Glu Lys Leu
65                  70                  75                  80

Ile Val Ala Leu Met Lys Pro Ser Arg Leu Tyr Asp Ala Tyr Glu Leu
                85                  90                  95

Lys His Ala Leu Lys Gly Ala Gly Thr Asn Glu Lys Val Leu Thr Glu
                100                 105                 110

Ile Ile Ala Ser Arg Thr Pro Glu Glu Leu Arg Ala Ile Lys Gln Val
            115                 120                 125

Tyr Glu Glu Glu Tyr Gly Ser Ser Leu Glu Asp Asp Val Val Gly Asp
        130                 135                 140

Thr Ser Gly Tyr Tyr Gln Arg Met Leu Val Val Leu Leu Gln Ala Asn
145                 150                 155                 160

Arg Asp Pro Asp Ala Gly Ile Asp Glu Ala Gln Val Glu Gln Asp Ala
                165                 170                 175

Gln Ala Leu Phe Gln Ala Gly Glu Leu Lys Trp Gly Thr Asp Glu Glu
                180                 185                 190

Lys Phe Ile Thr Ile Phe Gly Thr Arg Ser Val Ser His Leu Arg Lys
            195                 200                 205

Val Phe Asp Lys Tyr Met Thr Ile Ser Gly Phe Gln Ile Glu Glu Thr
        210                 215                 220

Ile Asp Arg Glu Thr Ser Gly Asn Leu Glu Gln Leu Leu Leu Ala Val
225                 230                 235                 240

Val Lys Ser Ile Arg Ser Ile Pro Ala Tyr Leu Ala Glu Thr Leu Tyr
                245                 250                 255

Tyr Ala Met Lys Gly Ala Gly Thr Asp Asp His Thr Leu Ile Arg Val
                260                 265                 270

Met Val Ser Arg Ser Glu Ile Asp Leu Phe Asn Ile Arg Lys Glu Phe
            275                 280                 285

Arg Lys Asn Phe Ala Thr Ser Leu Tyr Ser Met Ile Lys Gly Asp Thr
        290                 295                 300

Ser Gly Asp Tyr Lys Lys Ala Leu Leu Leu Leu Cys Gly Glu Asp Asp
305                 310                 315                 320
```